US011523736B2

(12) United States Patent
Yang et al.

(10) Patent No.: US 11,523,736 B2
(45) Date of Patent: Dec. 13, 2022

(54) SYSTEMS AND METHODS FOR PERFORMING GABOR OPTICAL COHERENCE TOMOGRAPHIC ANGIOGRAPHY

(71) Applicants: Victor X. D. Yang, North York (CA); Chaoliang Chen, Jiangsu (CN)

(72) Inventors: Victor X. D. Yang, North York (CA); Chaoliang Chen, Jiangsu (CN)

( * ) Notice: Subject to any disclaimer, the term of this patent is extended or adjusted under 35 U.S.C. 154(b) by 388 days.

(21) Appl. No.: 16/764,426

(22) PCT Filed: Nov. 16, 2018

(86) PCT No.: PCT/CA2018/051459
§ 371 (c)(1),
(2) Date: May 15, 2020

(87) PCT Pub. No.: WO2019/095069
PCT Pub. Date: May 23, 2019

(65) Prior Publication Data
US 2020/0352437 A1 Nov. 12, 2020

Related U.S. Application Data

(60) Provisional application No. 62/587,285, filed on Nov. 16, 2017.

(51) Int. Cl.
*A61B 3/12* (2006.01)
*G16H 30/40* (2018.01)
(Continued)

(52) U.S. Cl.
CPC .......... *A61B 3/1233* (2013.01); *A61B 3/0025* (2013.01); *A61B 3/102* (2013.01);
(Continued)

(58) Field of Classification Search
CPC ........ G16H 30/20; G16H 40/63; G16H 50/20; G16H 30/40; A61B 3/102; A61B 3/0025;
(Continued)

(56) References Cited

U.S. PATENT DOCUMENTS 7,712,898 B2 5/2010 Abramoff et al.
7,725,169 B2 5/2010 Boppart et al.
(Continued)

FOREIGN PATENT DOCUMENTS

WO 2017218738 A1 12/2017

OTHER PUBLICATIONS

Cernat, R. et al., Biomed. Opt. Express 8, 813-827 (2017).
(Continued)

*Primary Examiner* — Brenda C Bernardi
(74) *Attorney, Agent, or Firm* — Hill & Schumacher

(57) ABSTRACT

Systems and methods are provided for performing optical coherence tomography angiography for the rapid generation of en face images. According to one example embodiment, differential interferograms obtained using a spectral domain or swept source optical coherence tomography system are convolved with a Gabor filter, where the Gabor filter is computed according to an estimated surface depth of the tissue surface. The Gabor-convolved differential interferogram is processed to produce an en face image, without requiring the performing of a fast Fourier transform and k-space resampling. In another example embodiment, two interferograms are separately convolved with a Gabor filter, and the amplitudes of the Gabor-convolved interferograms are subtracted to generate a differential Gabor-convolved interferogram amplitude frame, which is then further processed to generate an en face image in the absence of performing a fast Fourier transform and k-space resampling. The example OCTA methods disclosed herein are shown to (Continued)

achieve faster data processing speeds compared to conventional OCTA algorithms.

20 Claims, 29 Drawing Sheets

(51) Int. Cl.
*A61B 3/00* (2006.01)
*A61B 3/10* (2006.01)
*A61B 5/00* (2006.01)
*G06T 7/00* (2017.01)
*G06T 11/00* (2006.01)

(52) U.S. Cl.
CPC ............ *A61B 5/0066* (2013.01); *A61B 5/489* (2013.01); *A61B 5/7214* (2013.01); *G06T 7/0012* (2013.01); *G06T 11/008* (2013.01); *G16H 30/40* (2018.01); *A61B 2562/0233* (2013.01); *A61B 2576/00* (2013.01); *G06T 2207/30041* (2013.01); *G06T 2207/30088* (2013.01); *G06T 2210/41* (2013.01); *G06T 2211/404* (2013.01)

(58) Field of Classification Search
CPC ... A61B 5/7257; A61B 5/7214; A61B 5/7207; A61B 3/1233; A61B 5/0066; A61B 5/026; A61B 5/489; A61B 5/14555; A61B 5/441; A61B 2562/0233; A61B 5/0042; A61B 2576/00; A61B 5/4222; A61B 5/0044; G06T 11/008; G06T 7/0012; G06T 2207/30041; G06T 2210/41; G06T 2207/30088; G06T 2211/404
See application file for complete search history.

(56) References Cited

U.S. PATENT DOCUMENTS

| | | | |
|---|---|---|---|
| 8,340,455 | B2 | 12/2012 | Rolland et al. |
| 8,687,856 | B2 | 4/2014 | Bower et al. |
| 8,750,615 | B2 | 6/2014 | Rollins et al. |
| 8,787,623 | B2 | 7/2014 | Bower et al. |
| 9,384,537 | B2 | 7/2016 | Sun et al. |
| 9,454,817 | B2 | 9/2016 | Clifton et al. |
| 2012/0236259 | A1 | 9/2012 | Abramoff et al. |
| 2013/0289882 | A1 | 10/2013 | Sharma et al. |
| 2015/0324966 | A1 | 11/2015 | Clifton et al. |
| 2016/0106314 | A1 | 4/2016 | Everett et al. |
| 2016/0278627 | A1 | 9/2016 | Huang et al. |
| 2016/0307314 | A1* | 10/2016 | Reisman ............ G06K 9/6215 |
| 2016/0317020 | A1 | 11/2016 | Liu et al. |

OTHER PUBLICATIONS

Murali, S., Doctoral Thesis, Gabor Domain Optical Coherence Microscopy, University of Central Florida, 2009.
Meemon, P. et al., Opt. Lett. 41, 508-511 (2013)G.
Gao, S. et al., Biomed. Opt. Exp. 8, 48-56 (2017).
Chitchian, S. et al., J. Biomed. Opt. 15, 046014-1-6 (2010).
Chen, Z., Biomed. Opt. Exp. 7, 3032-3048 (2016).
Rodrigues, P. et al., J. Biomed. Opt. 18, 126011-1-12 (2013).
Rolland, J. et al., Opt. Exp. 18, 3632-3642 (2010).
Costa, C. et al., J. Biomed. Opt. 20, 016012-1-10 (2015).
Shalbaf, F. et al., "An image processing pipeline for segmenting the retinal layers from optical coherence tomography images", 2013 28th International Conference on Image and Vision Computing New Zealand (2013).
Canavesi, A. et al., "3D wide field-of-view Gabor-domain optical coherence microscopy advancing real-time in-vivo imaging and metrology", Proc. SPIE 10053, Optical Coherence Tomography and Coherence Domain Optical Methods in Biomedicine XXI, 100530Z (2017).
International Search Report from PCT/CA2018/051459 dated Mar. 7, 2019.

* cited by examiner

Sparse matrix surface estimation
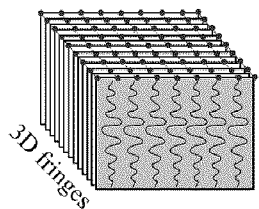
FIG. 4A
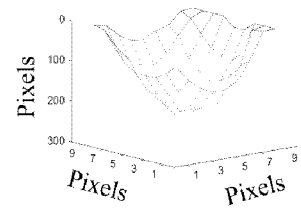
FIG. 4B
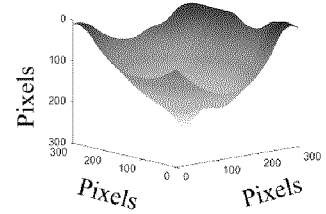
FIG. 4C
(a) Sub-spectral band:  FIG. 5A
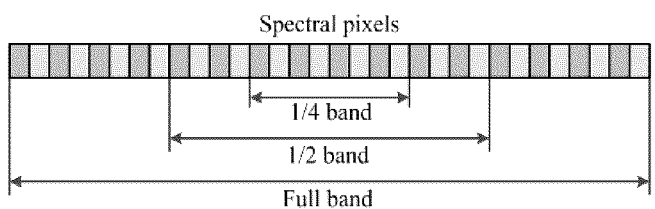
(b) Sub-sampling:  FIG. 5B
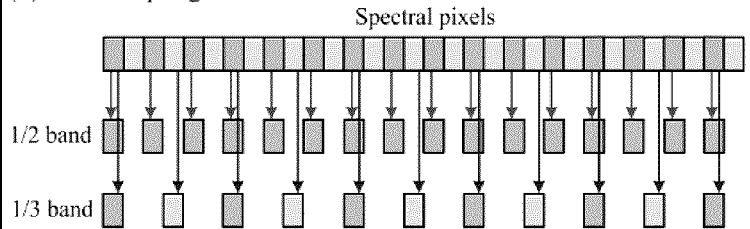
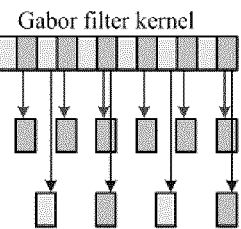
(c) Skipped convolution:  FIG. 5C
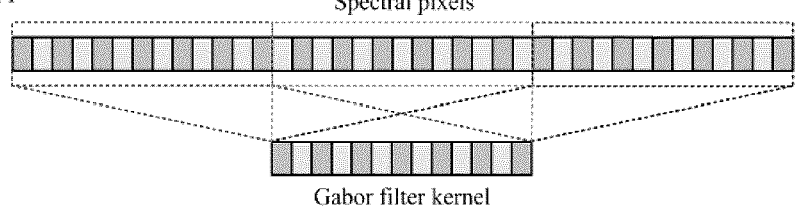

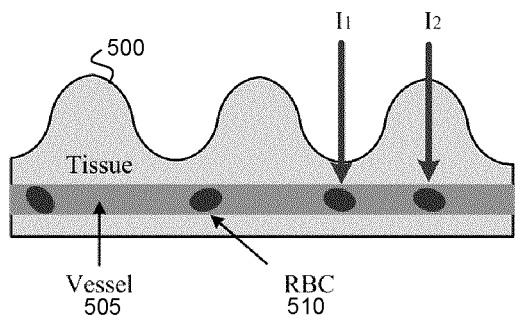
FIG. 6A
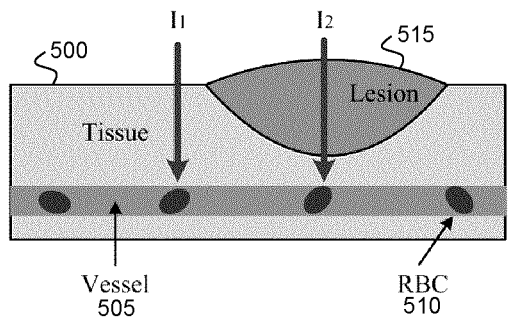
FIG. 6B
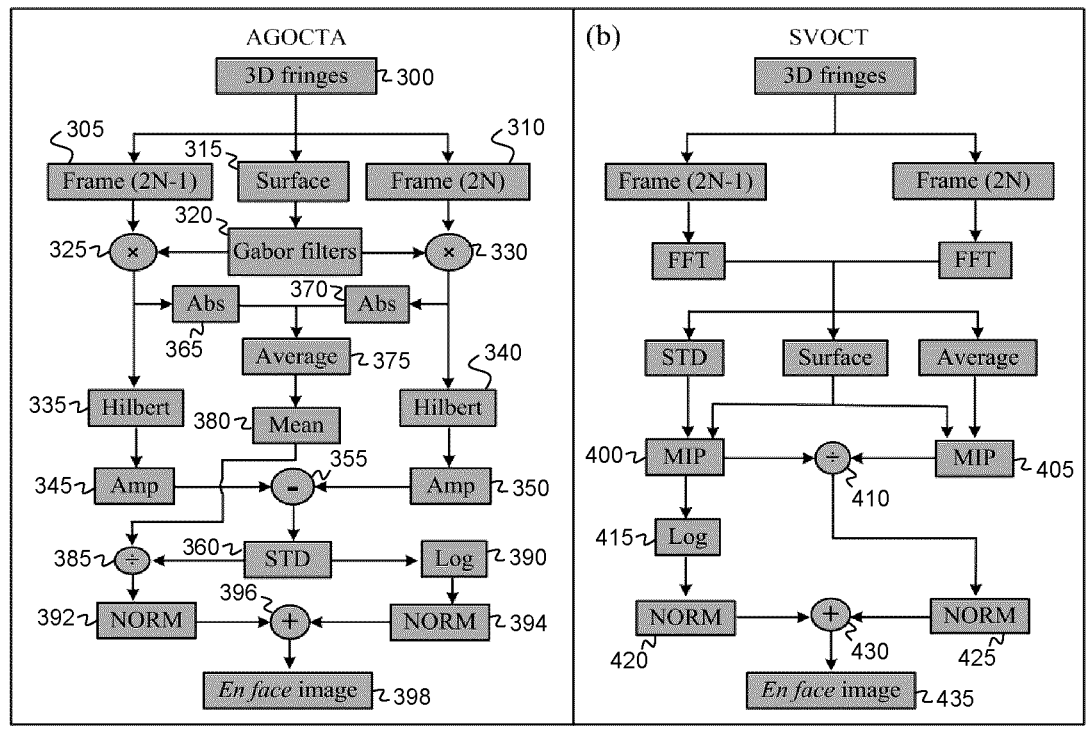
FIG. 7A
FIG. 7B

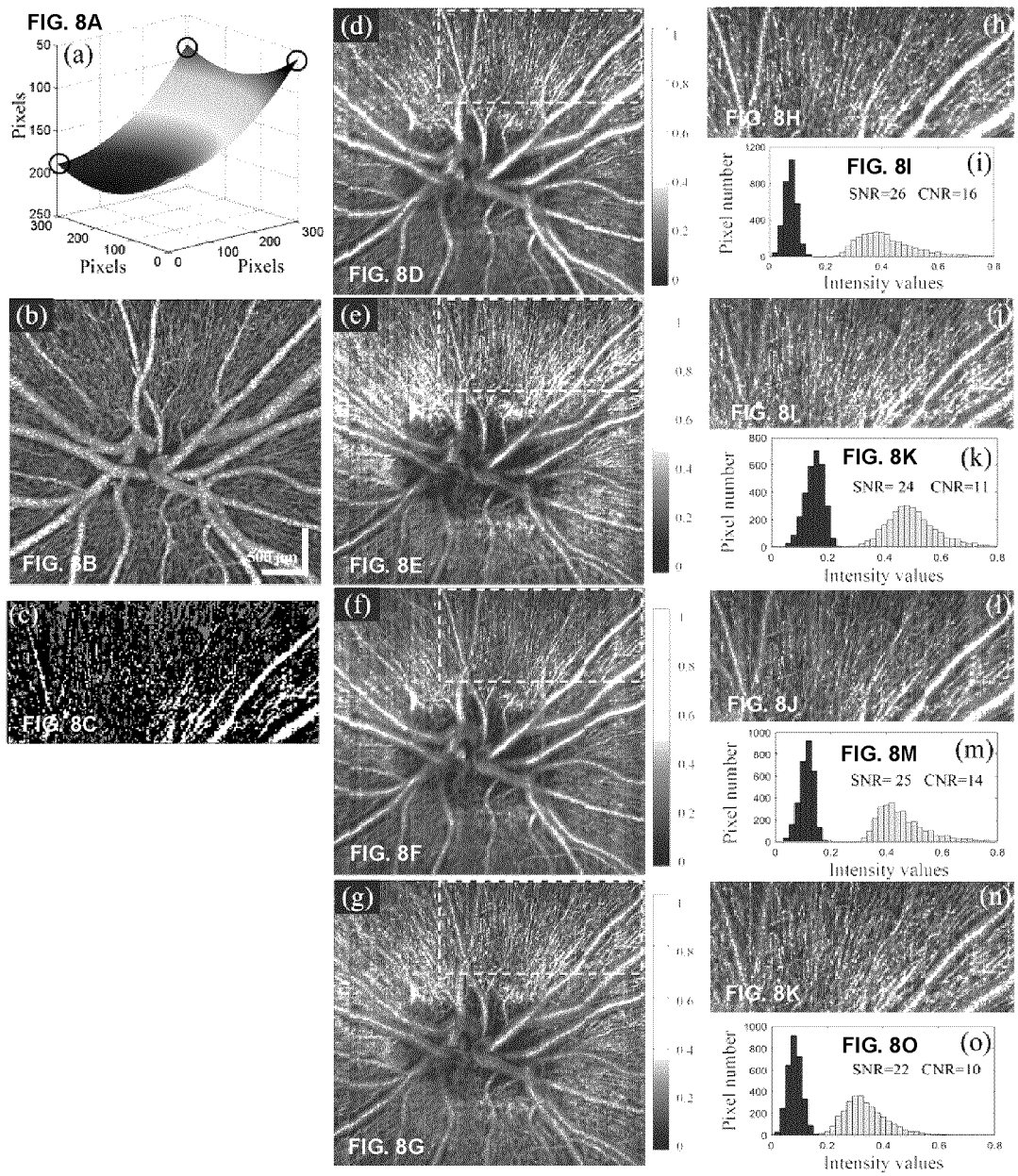

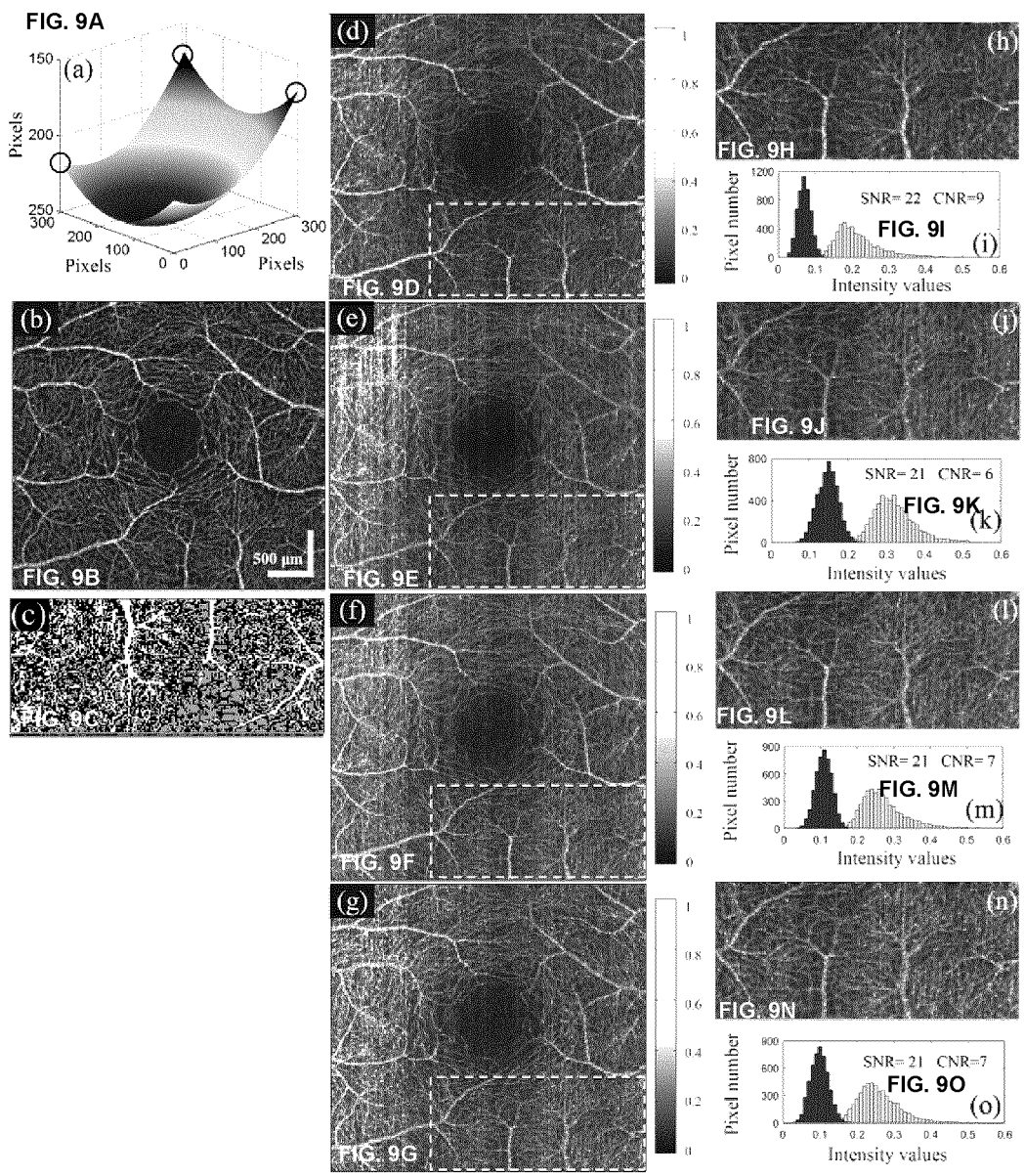

|  | CPU processing time (ms) | | | | |
| --- | --- | --- | --- | --- | --- |
|  | GOCTA | SVOCT | UHS-OMAG | SSADA$^Y$ | SSADA$^{X-Y}$ |
| Remove DC | - | 7.6 | 7.6 | 7.6 | 15.2 |
| Resampling | - | 198.2 | 198.2 | 198.2 | 396.4 |
| Dispersion compensation | - | 71.2 | 71.2 | 71.2 | 168.2 |
| Fringes subtraction | 37.0 | - | 37.0 | - | - |
| Surface calculation | 8.4 | - | - | - | - |
| Gabor filter | 30.4 | - | - | - | - |
| FFT | - | 68.6 | 34.3 | 274.4 | 548.8 |
| Image alignment | - | 116.6 | - | 116.6 | 233.2 |
| STD(or variance) | 10.7 | 49.5 | - | - | - |
| Decorrelation | - | - | - | 200.3 | 400.6 |
| Mean projection | - | 11.3 | 11.3 | 11.3 | 22.6 |
| Averaging | - | - | - | - | 17.8 |
| Total (ms) | 86.5 | 535.9 | 372.5 | 892.5 | 1802.8 |

FIG. 10A

|  | Processing time (s) | | | |
| --- | --- | --- | --- | --- |
|  | GOCTA | SVOCT | UHS-OMAG | SSADA$^Y$ |
| Only CPU | 26.2 | 141.2 | 91.5 | 288.6 |
| Computation steps by CPU | Surface calculation | Remove DC<br>Resampling<br>Dispersion compensation<br>Image alignment | Remove DC<br>Resampling<br>Dispersion compensation | Remove DC<br>Resampling<br>Dispersion compensation<br>Image alignment |
| CPU's time | 0.008 | 98.7 | 73.8 | 98.7 |
| Computation steps by GPU | Fringes subtraction<br>Gabor filter<br>STD | FFT<br>Variance<br>Mean projection | Fringes subtraction<br>FFT<br>Mean projection | FFT<br>Decorrelation<br>Mean projection |
| GPU's time | 8.5 | 14.5 | 10.6 | 39.3 |
| Total time (s) | 8.5 | 113.2 | 84.4 | 138.0 |

FIG. 10B

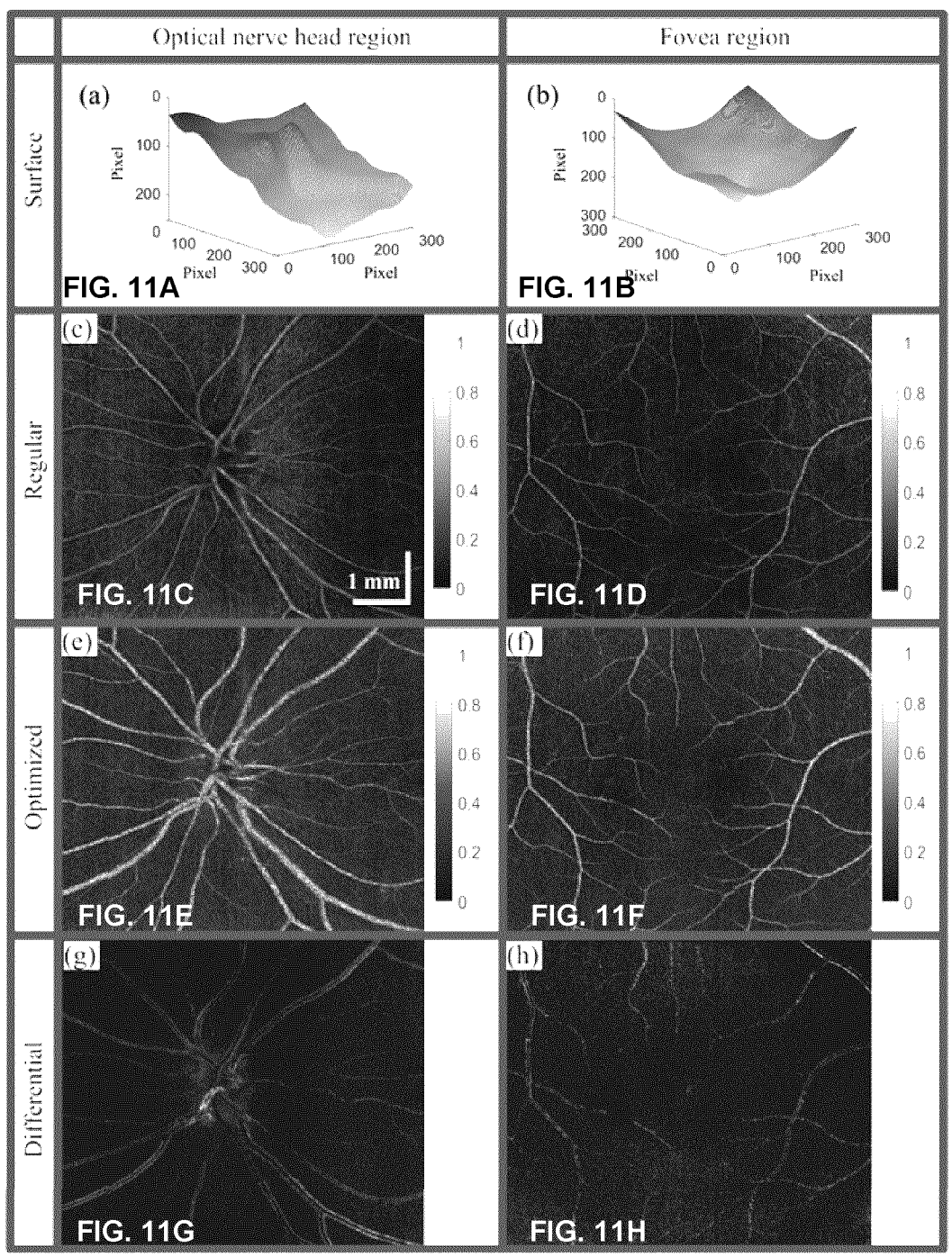

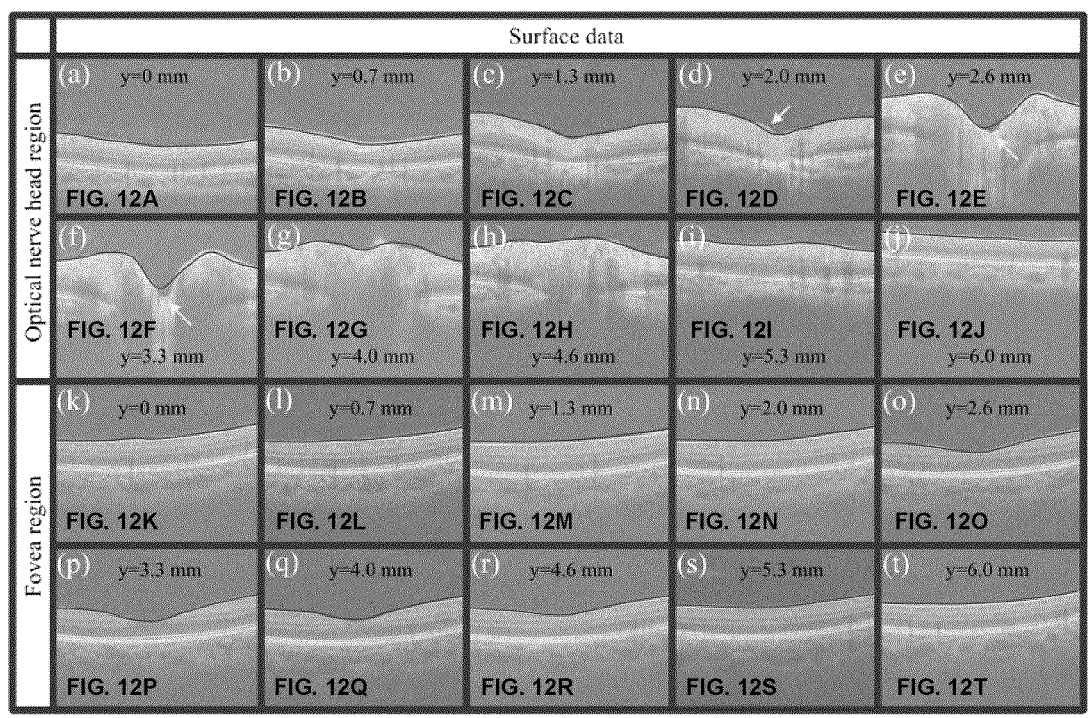

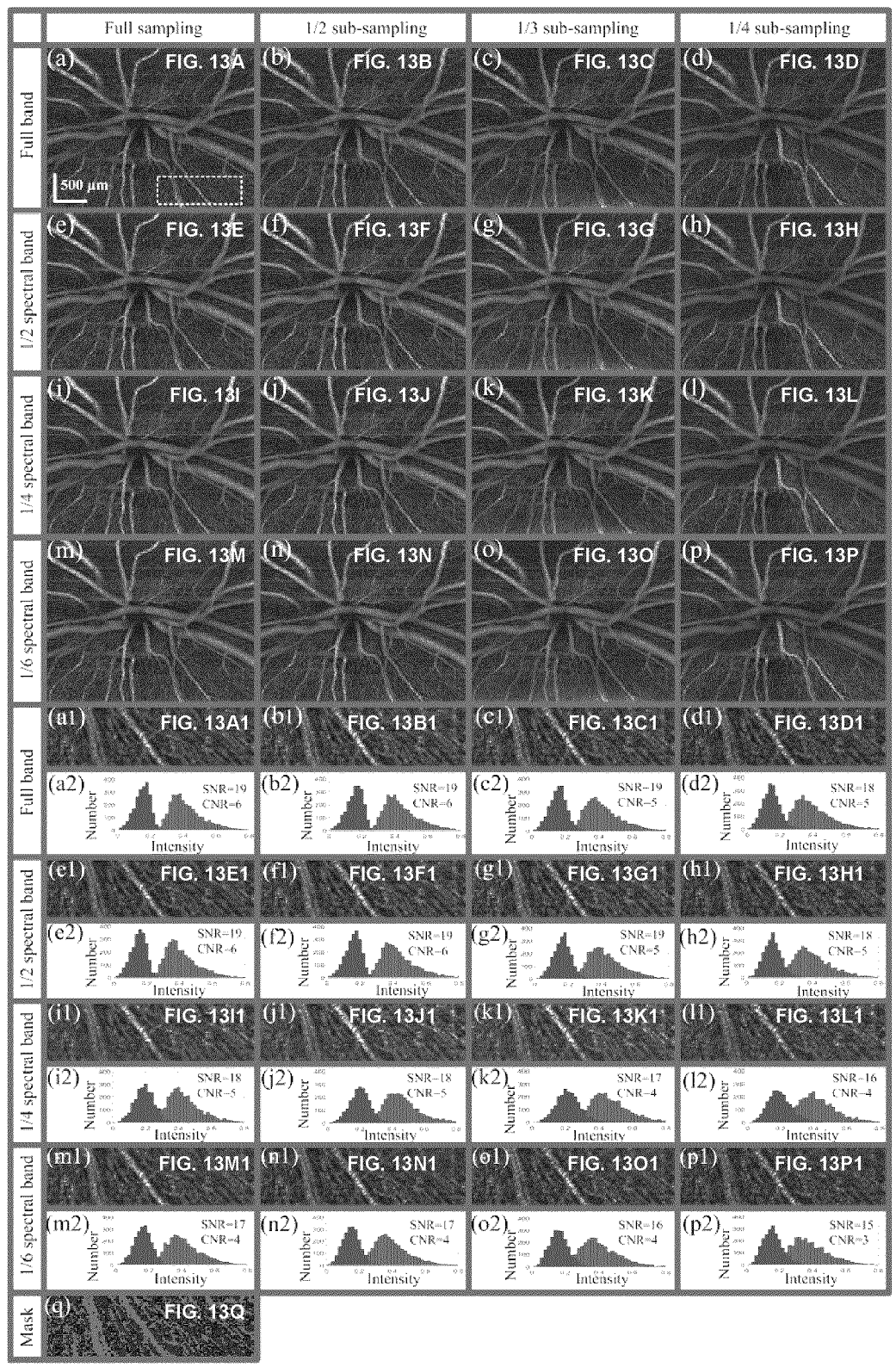

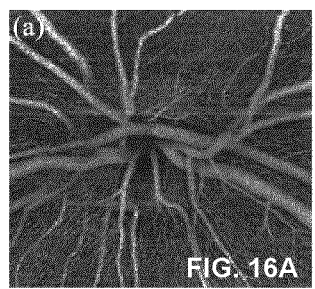
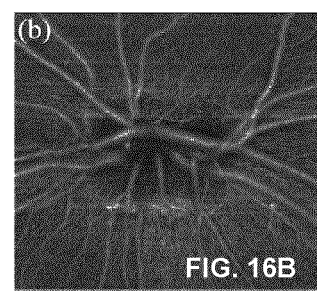
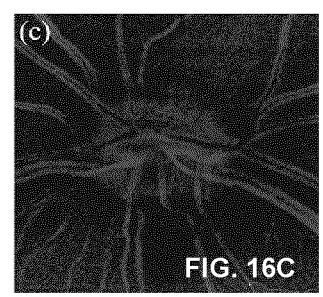
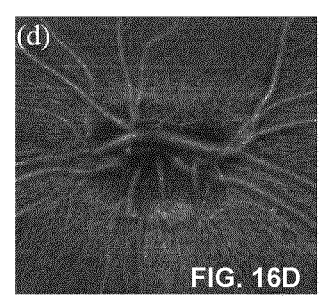
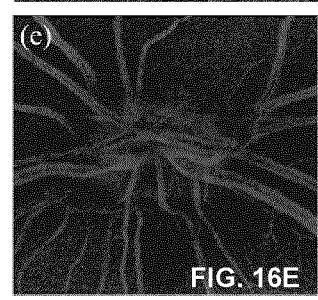
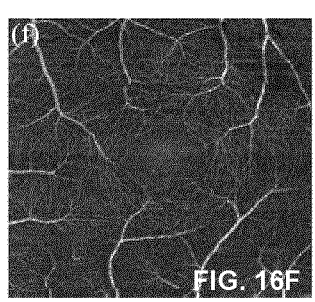
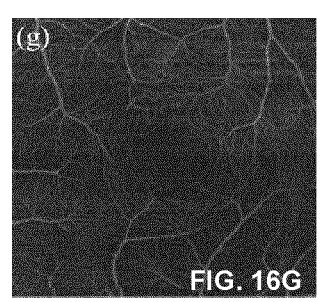
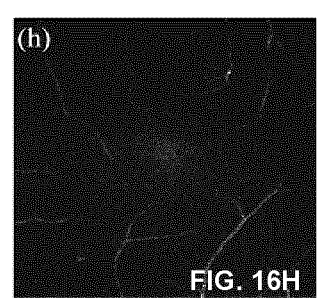
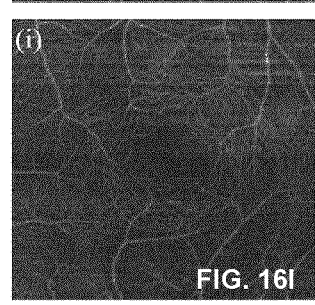
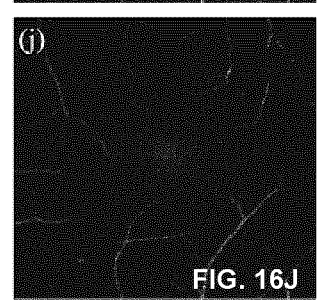

|     |                  | 3D data processing time (s) | | | |
| --- | --- | --- | --- | --- | --- |
|     |                  | Full band | 1/2 sampling band | 1/3 sampling band | 1/4 sampling band |
| CPU | Full band        | 27.1 | 12.5 | 11.4 | 10.8 |
|     | 1/2 spectral band | 14.6 | 6.3 | 5.6 | 5.3 |
|     | 1/4 spectral band | 7.4 | 3.2 | 2.9 | 2.8 |
|     | 1/6 spectral band | 4.7 | 2.0 | 1.9 | 1.8 |
| GPU | Full band        | 11.1 | 6.9 | 5.1 | 4.2 |
|     | 1/2 spectral band | 7.4 | 4.3 | 3.3 | 2.9 |
|     | 1/4 spectral band | 4.5 | 2.9 | 2.5 | 2.2 |
|     | 1/6 spectral band | 3.5 | 2.5 | 2.2 | 2.0 |

FIG. 18

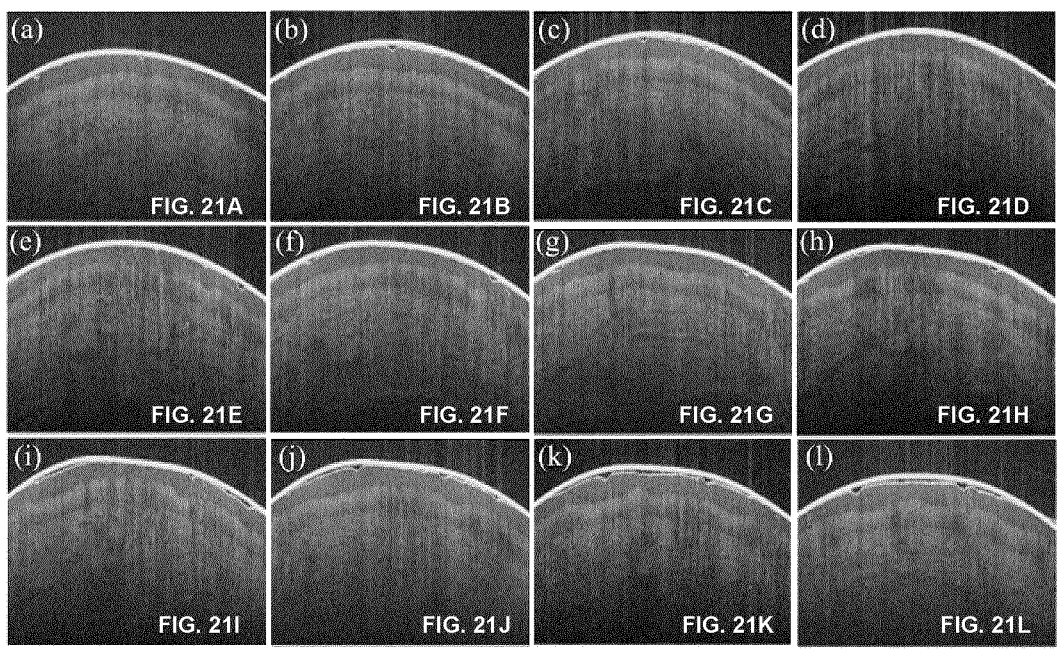

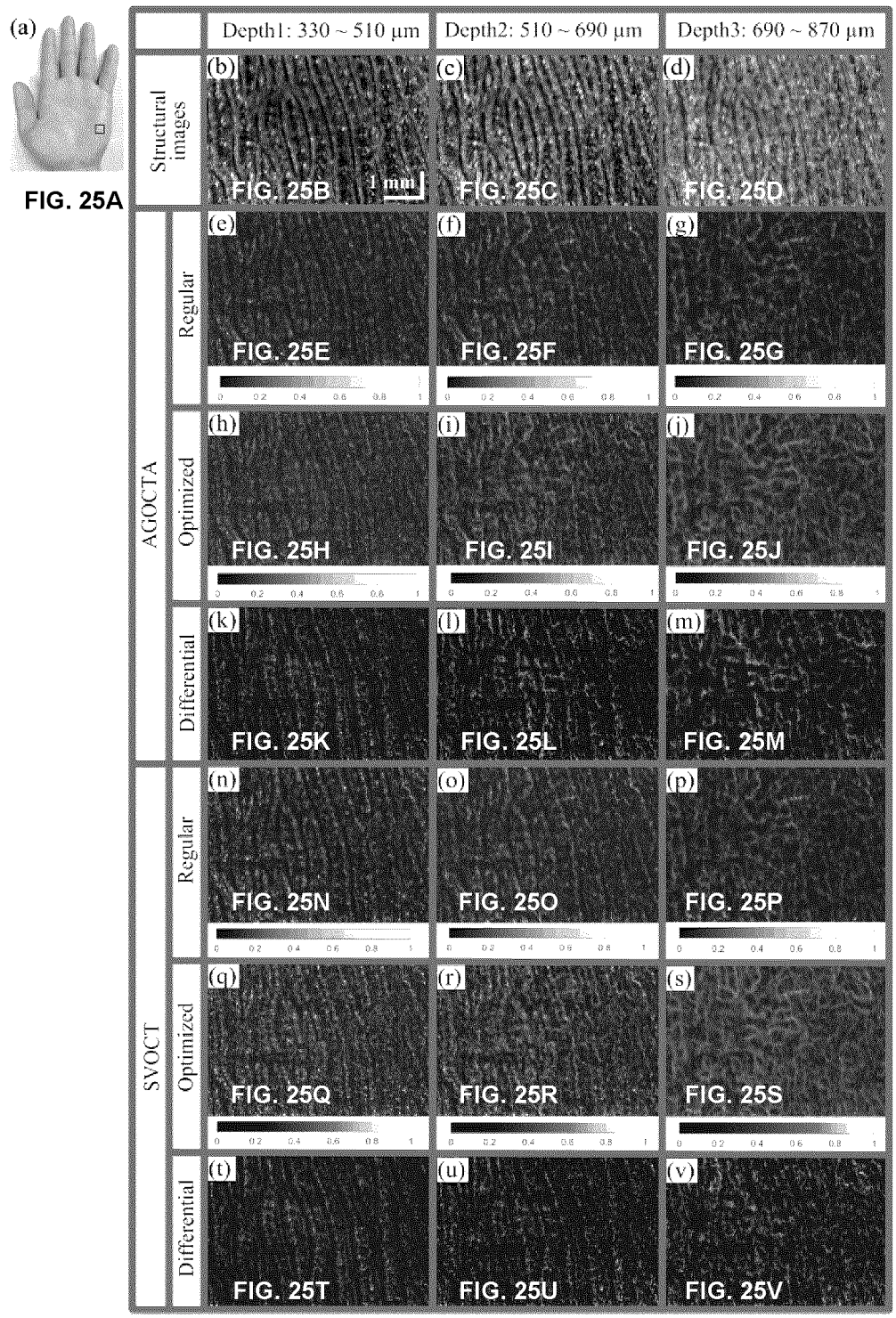

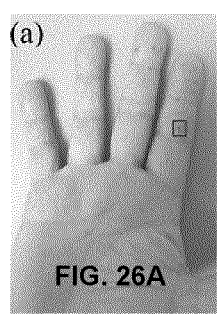
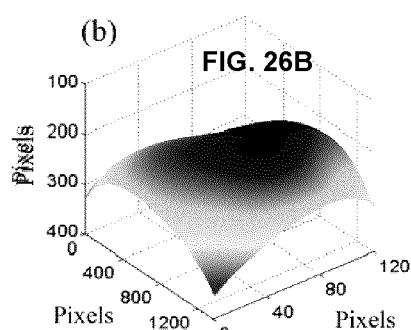
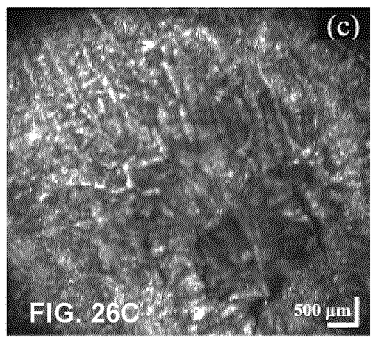
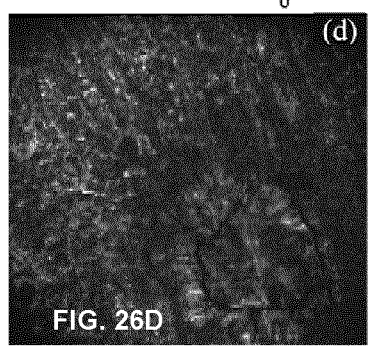
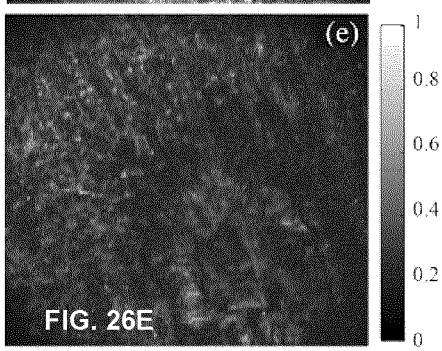
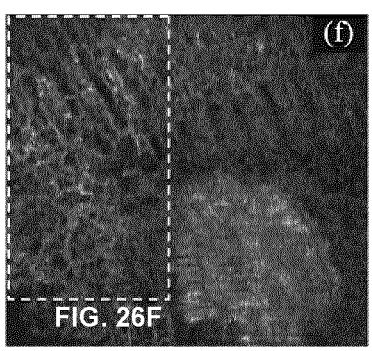
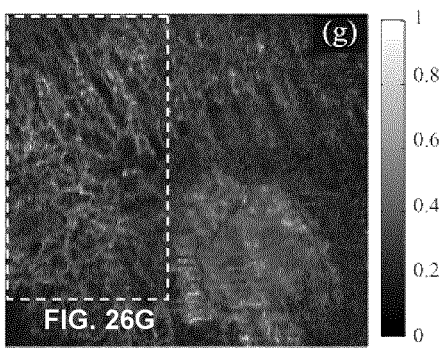
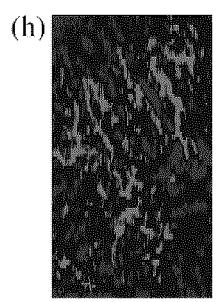
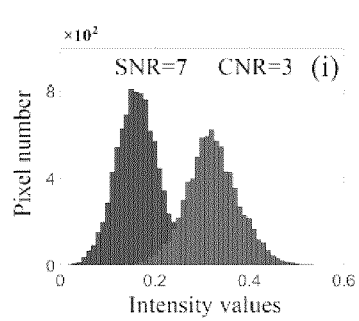
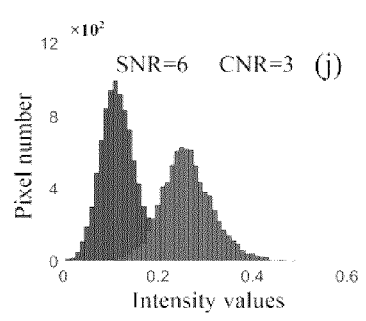
FIG. 26H      FIG. 26I      FIG. 26J Table 1. 3D data processing time of sub spectral bands and sub sampling band

|  |  | 3D data processing time (s) | | | |
| --- | --- | --- | --- | --- | --- |
|  |  | Full band | 1/2 spectral band | 1/4 spectral band | 1/6 sampling band |
| CPU | Full band | 49.1 | 24.9 | 13.5 | 9.8 |
| | 1/2 sampling band | 15.4 | 8.4 | 5.1 | 3.8 |
| | 1/3 sampling band | 12.7 | 7.0 | 4.1 | 3.2 |
| GPU | Full band | 17.3 | 9.1 | 4.8 | 3.1 |
| | 1/2 sampling band | 7.5 | 4.1 | 2.1 | 1.5 |
| | 1/3 sampling band | 4.9 | 2.5 | 1.5 | 1.2 |

FIG. 27

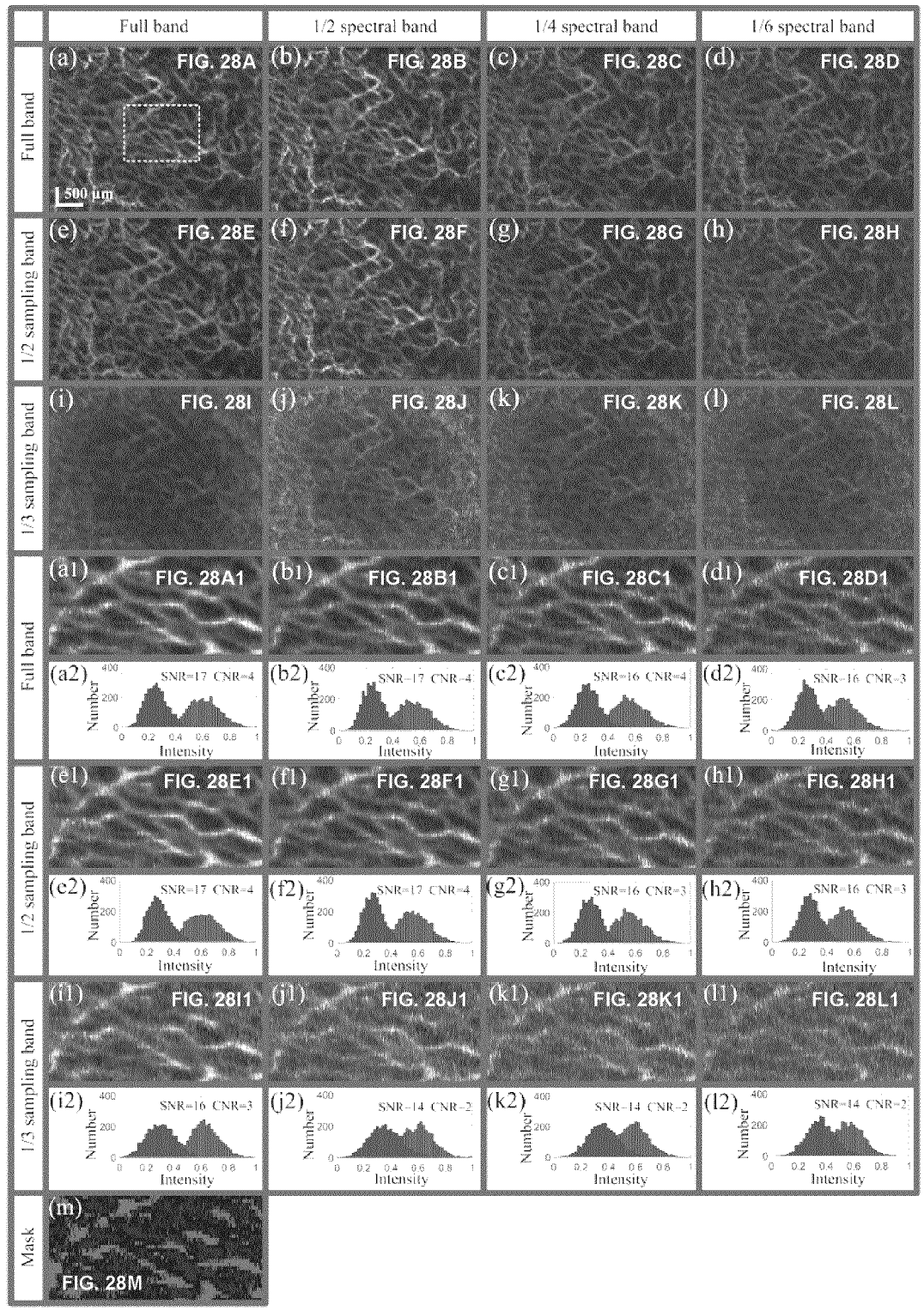

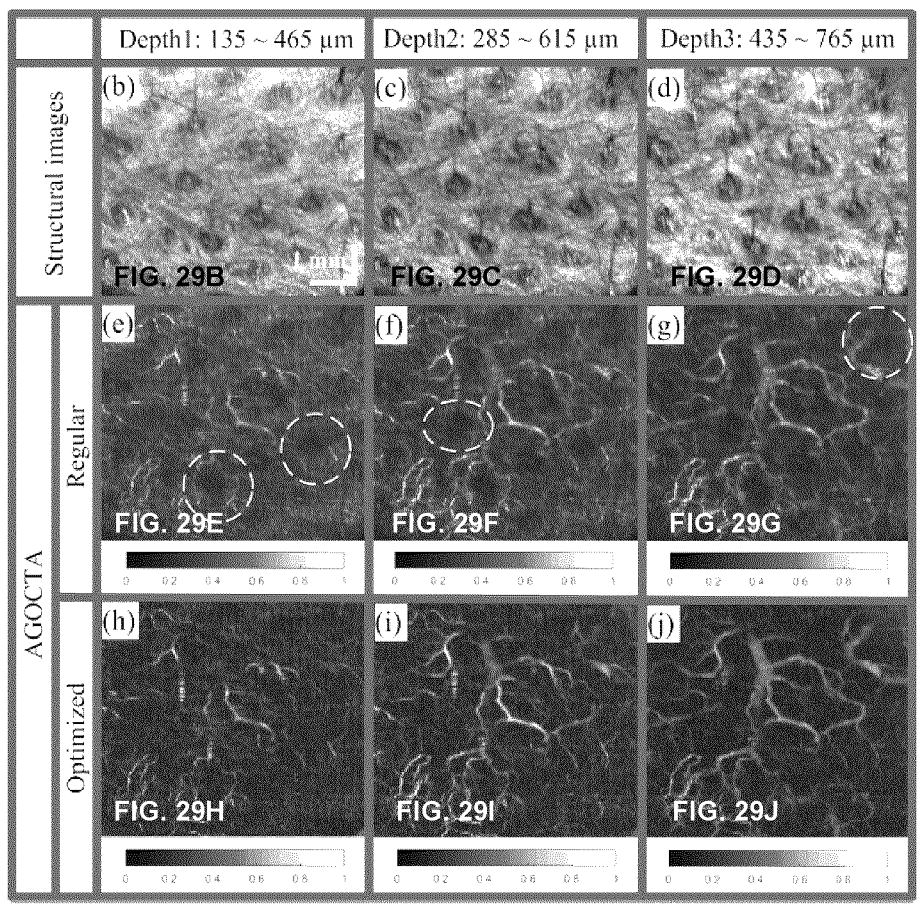
FIG. 29A FIG. 29B FIG. 29C FIG. 29D FIG. 29E FIG. 29F FIG. 29G FIG. 29H FIG. 29I FIG. 29J

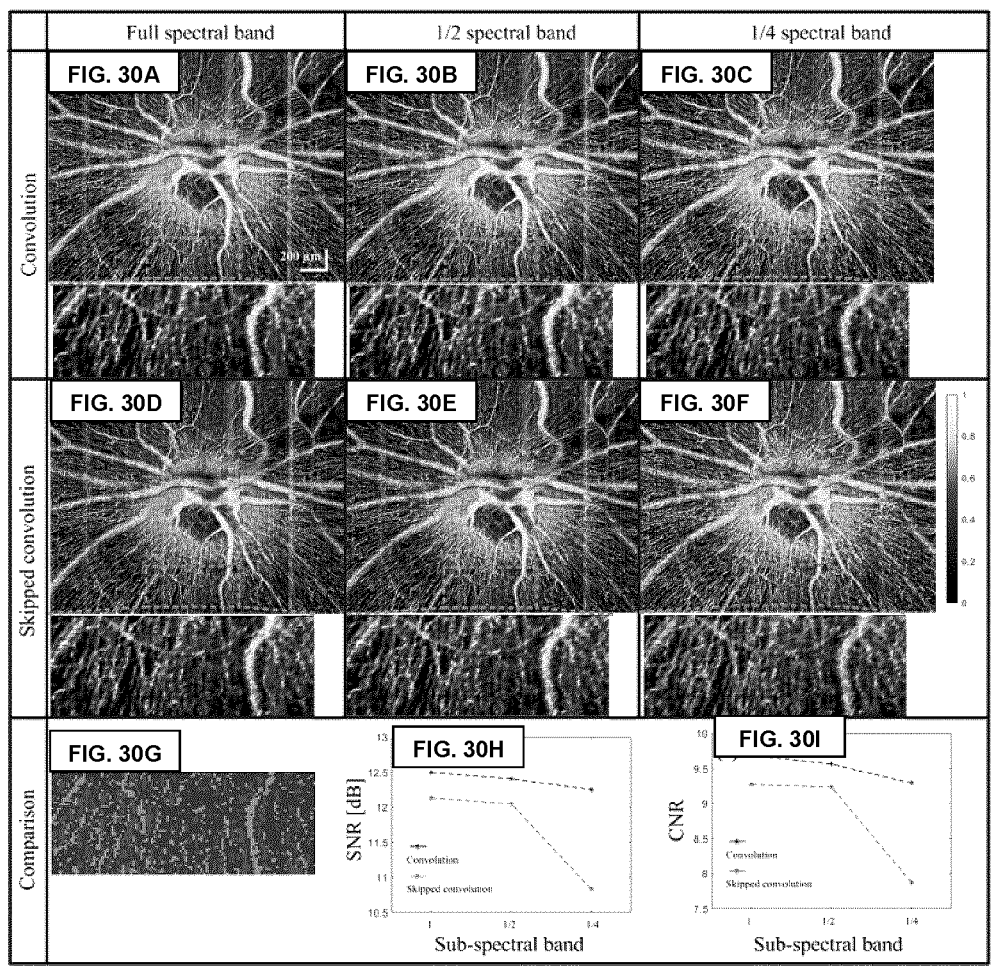

SYSTEMS AND METHODS FOR PERFORMING GABOR OPTICAL COHERENCE TOMOGRAPHIC ANGIOGRAPHY

CROSS-REFERENCE TO RELATED APPLICATION

This application is a National Phase application claiming the benefit of the international PCT Patent Application No. PCT/CA2018/051459, filed on Nov. 16, 2018, in English, which claims priority to U.S. Provisional Application No. 62/587,285, titled "SYSTEMS AND METHODS FOR PERFORMING GABOR OPTICAL COHERENCE TOMOGRAPHIC ANGIOGRAPHY" and filed on Nov. 16, 2017, the entire contents of which are incorporated herein by reference.

BACKGROUND

The present disclosure relates to optical coherence tomography angiography. The optical coherence tomography (OCT) technique, proposed in 1990s, is an emerging imaging modality for medical diagnostics and treatments. OCT is an optical imaging modality that produces depth-resolved images of sub-surface tissue structures using optical interference. Light emitted by a spatially coherent light-source is split between a reference beam and a sample probing beam. Backscattered light from structures within the sample is collected and combined with the reference beam, and the resulting interference is detected and processed to generate a depth profile of the sample. OCT may be performed according to several different implementations. Generally, OCT systems are classified as either time-domain OCT (TD-OCT) or frequency-domain optical OCT. The latter, frequency domain OCT, is often implemented as either spectral domain OCT (SD-OCT) or swept-source OCT (SS-OCT).

Due to the advantages of non-invasiveness, high resolution and high imaging speed, OCT is widely used for various tissue, e.g. human retina, brain, cardiology and dermatology. In addition to microstructural imaging, OCT based microvascular imaging algorithms are also used widely in medical imaging and play an increasingly important role. The first algorithm for extracting blood flow information is optical Doppler tomography (ODD or color Doppler OCT (CDOCT) which is able to calculate the axial velocity component of moving scattering particles.

Morphological OCT microvasculature imaging, collectively termed OCT angiography (OCTA), has also been developed. In general, OCTA algorithms available now can be divided into two categories according to processing mode. The first is inter-line mode, such as Doppler variance phase resolved (DVPR), intensity-based modified Doppler variance (IBDV), optical micro-angiography (OMAG). For inter-line mode, the blood flow information was extracted from one frame of interference fringes at each position. For DVPR and IBDV, the statistical information of a small window was calculated to contrast microvasculature, which needs high A-line density. For OMAG, a piezo-stage was used in reference arm for modulating of interference fringes, which increased complexity of OCT setup.

The second processing mode is inter-frame, which extracts blood flow information from multi-frames of structural images at each position, such as phase variance OCT (PVOCT), speckle variance OCT (SVOCT), correlation mapping OCT (cmOCT), split-spectrum amplitude-decorrelation angiography (SSADA) and differential standard deviation of log-scale intensity (DSDLI), and ultrahigh sensitivity optical micro-angiography (UHS-OMAG). For this mode, the sensitivity for microvasculature detection can be improved due to the time interval between two frames is longer than that between two A-scans, but the motion artifacts are also more significant due to increase of time interval. PVOCT, SVOCT, cmOCT, SSADA, and DSDLI obtain blood vessel contrast by calculating statistical information from either phase or intensity images in spatial domain. PVOCT calculates the variance of phase difference between two frames. SVOCT and DSDLI calculate the variances of intensity and the differential intensity between two frames, respectively. Both cmOCT and SSADA calculate the decorrelation coefficients, but in SSADA, the full spectrum is divided into four sub-bands to improve microvascular image quality. For UHS-OMAG, the OMAG algorithm is performed in the slow scanning direction and blood flow signal is calculated from both amplitude and phase signals, resulting in an improvement of sensitivity.

Recently, parallel imaging and wide field imaging have become more prevalent, resulting in a dramatic increase of data quantity which poses a challenge for real time imaging even when using GPU for data processing.

SUMMARY

Systems and methods are provided for performing optical coherence tomography angiography for the rapid generation of en face images. According to one example embodiment, differential interferograms obtained using a spectral domain or swept source optical coherence tomography system are convolved with a Gabor filter, where the Gabor filter is computed according to an estimated surface depth of the tissue surface. The Gabor-convolved differential interferogram is processed to produce an en face image, without requiring the performing of a fast Fourier transform and k-space resampling. In another example embodiment, two interferograms are separately convolved with a Gabor filter, and the amplitudes of the Gabor-convolved interferograms are subtracted to generate a differential Gabor-convolved interferogram amplitude frame, which is then further processed to generate an en face image in the absence of performing a fast Fourier transform and k-space resampling. The example OCTA methods disclosed herein are shown to achieve faster data processing speeds compared to conventional OCTA algorithms.

Accordingly, in one aspect, there is provided a method of generating an en face angiography image via optical coherence tomography, the method comprising:
  employing a spectral domain or swept source optical coherence tomography system to scan a spatial region comprising a tissue surface and to detect at least a first spectral interferogram frame and a second spectral interferogram frame;
  processing the first spectral interferogram frame and the second spectral interferogram frame via subtraction to generate a differential spectral interferogram frame;
  performing a convolution of a Gabor filter with the differential spectral interferogram frame, thereby obtaining a Gabor-convolved differential spectral interferogram frame, wherein the Gabor filter is computed, on a per-pixel basis, based on an estimated depth of the tissue surface; and
  processing the Gabor-convolved differential spectral interferogram frame to generate the en face angiography image, wherein the Gabor-convolved differential spectral interferogram frame is processed in the absence of performing a fast Fourier transform and k-space resampling.

In another aspect, there is provided a system for generating an en face angiography image via optical coherence tomography, the system comprising:

a spectral domain or swept source optical coherence tomography system; and control and processing circuitry operatively coupled to the optical coherence tomography system, the control and processing circuitry comprising a processor and a memory, wherein the processor is configured to execute instructions stored in the memory for performing the steps of:

controlling the optical coherence tomography system to scan a spatial region comprising a tissue surface and to detect at least a first spectral interferogram frame and a second spectral interferogram frame;

processing the first spectral interferogram frame and the second spectral interferogram frame via subtraction to generate a differential spectral interferogram frame;

performing a convolution of a Gabor filter with the differential spectral interferogram frame, thereby obtaining a Gabor-convolved differential spectral interferogram frame, wherein the Gabor filter is computed, on a per-pixel basis, based on an estimated depth of the tissue surface; and processing the Gabor-convolved differential spectral interferogram frame to generate the en face angiography image, wherein the Gabor-convolved differential spectral interferogram frame is processed in the absence of performing a fast Fourier transform and k-space resampling.

In another aspect, there is provided a method of generating an en face angiography image via optical coherence tomography, the method comprising:

employing a spectral domain or swept source optical coherence tomography system to scan a spatial region comprising a tissue surface and to detect at least a first spectral interferogram frame and a second spectral interferogram frame;

performing a convolution of a Gabor filter with the first spectral interferogram frame and the second spectral interferogram frame, thereby obtaining a first Gabor-convolved spectral interferogram frame and a second Gabor-convolved spectral interferogram frame, respectively, wherein the Gabor filter is computed, on a per-pixel basis, based on an estimated depth of the tissue surface;

processing the first Gabor-convolved spectral interferogram frame and the second Gabor-convolved spectral interferogram frame to obtain amplitudes thereof, thereby obtaining a first Gabor-convolved spectral interferogram amplitude frame and a second Gabor-convolved spectral interferogram amplitude frame, respectively, processing the first Gabor-convolved spectral interferogram amplitude frame and the second Gabor-convolved spectral interferogram amplitude frame via subtraction to generate a differential Gabor-convolved spectral interferogram amplitude frame; and processing the differential Gabor-convolved spectral interferogram amplitude frame to generate the en face angiography image, wherein the differential Gabor-convolved spectral interferogram amplitude frame is processed in the absence of performing a fast Fourier transform and k-space resampling.

In another aspect, there is provided a system for generating an en face angiography image via optical coherence tomography, the system comprising:

a spectral domain or swept source optical coherence tomography system; and control and processing circuitry operatively coupled to the optical coherence tomography system, the control and processing circuitry comprising a processor and a memory, wherein the processor is configured to execute instructions stored in the memory for performing the steps of:

controlling the optical coherence tomography system to scan a spatial region comprising a tissue surface and to detect at least a first spectral interferogram frame and a second spectral interferogram frame;

performing a convolution of a Gabor filter with the first spectral interferogram frame and the second spectral interferogram frame, thereby obtaining a first Gabor-convolved spectral interferogram frame and a second Gabor-convolved spectral interferogram frame, respectively, wherein the Gabor filter is computed, on a per-pixel basis, based on an estimated depth of the tissue surface;

processing the first Gabor-convolved spectral interferogram frame and the second Gabor-convolved spectral interferogram frame to obtain amplitudes thereof, thereby obtaining a first Gabor-convolved spectral interferogram amplitude frame and a second Gabor-convolved spectral interferogram amplitude frame, respectively, processing the first Gabor-convolved spectral interferogram amplitude frame and the second Gabor-convolved spectral interferogram amplitude frame via subtraction to generate a differential Gabor-convolved spectral interferogram amplitude frame; and processing the differential Gabor-convolved spectral interferogram amplitude frame to generate the en face angiography image, wherein the differential Gabor-convolved spectral interferogram amplitude frame is processed in the absence of performing a fast Fourier transform and k-space resampling.

In another aspect, there is provided a method of performing texture noise suppression of a first spectral variance optical coherence tomography en face image, the first spectral variance optical coherence tomography en face image having been generated based on a first spectral interferogram frame and a second spectral interferogram frame, the method comprising:

dividing the first spectral variance optical coherence tomography en face image by a mean intensity projection of an average of the first spectral interferogram frame and the second spectral interferogram frame, thereby obtaining a second spectral variance optical coherence tomography en face image; and obtaining a texture-noise-suppressed spectral variance optical coherence tomography image by summing a normalization of a logarithm of the first spectral variance optical coherence tomography en face image and a normalization of the second spectral variance optical coherence tomography en face image.

In another aspect, there is provided a system for performing texture noise suppression of a spectral variance optical coherence tomography en face images, the system comprising:

a spectral domain or swept source optical coherence tomography system; and control and processing circuitry operatively coupled to the optical coherence tomography system, the control and processing circuitry comprising a processor and a memory, wherein the processor is configured to execute instructions stored in the memory for performing the steps of:

controlling the optical coherence tomography system to scan a spatial region comprising a tissue surface and to detect at least a first spectral interferogram frame and a second spectral interferogram frame;

processing the first spectral interferogram frame and the second spectral interferogram frame to generate a first spectral variance optical coherence tomography en face image therefrom;

dividing the first spectral variance optical coherence tomography en face image by a mean intensity projection of an average of the first spectral interferogram frame and the second spectral interferogram frame, thereby obtaining a second spectral variance optical coherence tomography en face image; and obtaining a texture-noise-suppressed spectral variance optical coherence tomography image by summing a normalization of a logarithm of the first spectral variance optical coherence tomography en face image and a normalization of the second spectral variance optical coherence tomography en face image.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 4A-4C show an illustration of the steps of surface calculation based on a plurality of A-scans that sample the surface.

FIGS. 5A-5C illustrate example methods of sub-spectral-band, sub-sampling, and skipped convolution processing, respectively.

FIGS. 6A and 6B illustrate an example cause of texture noise for (A) finger or palm print and (B) skin lesion. "RBC" is a red blood cell.

FIGS. 7A and 7B are flow charts illustrating example methods of data processing steps for (A) AGOCTA with optional texture noise removal, and (B) SVOCT with texture noise removal. The orange steps illustrate methods of texture noise removal. Abs, Amp and NORM are the operator for calculating absolute values, amplitude and normalization, Hilbert and MIP are Hilbert transform and mean intensity projection, respectively.

FIGS. 8A-8O provide a comparison of the microvascular images at optical nerve head region. (a) The structural surface calculated by using Eq. 3, the three corners marked by black circles were calculated by FFT. (b) The images outputted from a commercial system. (c) The mask for dynamic blood flow signals (red) and background (blue) on a local region marked by the dashed rectangles in (d)-(g). (d)-(g) are the microvascular images obtained by GOCTA, SVOCT, UHS-OMAG and SSADA, respectively. (h), (j), (l) and (n) are the zoomed-in local regions marked by the dashed white rectangles in (d)-(g), respectively. (i), (k), (m) and (o) are the histograms of the intensity values covered by mask (c), where the red and the blue represent dynamic flow signal and background, respectively. (b) and (d)-(g) share the scale bar.

FIGS. 9A-9O provide a comparison of the microvascular images at fovea region. (a) The structural surface calculated by using Eq. 3, the three corners marked by black circles were calculated by FFT. (b) The images outputted from the commercial system. (c) The mask for dynamic blood flow signals (red) and background (blue) on a local region marked by the dashed rectangles in (d)-(g). (d)-(g) are the microvascular images obtained by GOCTA, SVOCT, UHS-OMAG and SSADA, respectively. (h), (j), (l) and (n) are the zoomed-in local regions marked by the dashed white rectangles in (d)-(g), respectively. (i), (k), (m) and (o) are the histograms of the intensity values covered by mask (c), where the red and the blue represent dynamic flow signal and background, respectively. (b) and (d)-(g) share the scale bar.

FIG. 10A is a table comparing the data processing time for each two B-scans from the same position.

FIG. 5B is a table comparing the data processing time for entire 3D (608×2048×304) dataset by CPU and GPU.

FIGS. 11A-11H show results from retinal imaging of a healthy volunteer, for which a local region of 6×6 mm$^2$ was scanned on both optical nerve head region and fovea region. (a) and (b) are the surface data obtained by using an example implementation of the GOCTA method described herein. (c) and (d) are the regular en face microvascular images for optical head nerve region and fovea region, respectively. (e) and (f) are the optimized microvascular images. (g) and (h) are the differential images obtained by subtracting (e) by (c), (f) by (d), respectively. (c)-(h) share the same scale bar.

FIGS. 12A-12T show surface data (red curves) obtained by using an example implementation of the present GOCTA method. (a)-(j) are the cross sectional structural images with surface data for optical nerve head region at positions of 0 mm, 0.7 mm, 1.3 mm, 2.0 mm, 2.6 mm, 3.3 mm, 4.0 mm, 4.6 mm, 5.3 mm and 6.0 mm. (k)-(t) are the cross sectional structural images with surface data for fovea region at positions of 0 mm, 0.7 mm, 1.3 mm, 2.0 mm, 2.6 mm, 3.3 mm, 4.0 mm, 4.6 mm, 5.3 mm and 6.0 mm.

FIGS. 13A-13Q show microvascular images of sub spectral band and sub sampling band on optical nerve head region. (a)-(p) are en face images with different spectral bands and different sampling bands. (a1)-(p1) are the zoomed local images in the marked region by a dashed rectangle in (a)-(p). (a2)-(p2) are the histograms of the pixel intensities in (a1)-(p1) covered by mask (q), where red and blue represent dynamic and static signals, respectively. (a)-(p) share the same scale bar.

FIGS. 16A-16J show microvascular images obtained by GOCTA, SVOCT and OMAG on ¼ spectral band and ½ sampling band. (a), (b) and (d) are images on optical head nerve region obtained by GOCTA, SVOCT and OMAG, respectively. (c) and (e) are the differential images of subtracting (a) by (b) and (a) by (d). (f), (g) and (i) are images on fovea region obtained by GOCTA, SVOCT and OMAG. (h) and (j) are the differential images of subtracting (f) by (g) and (f) by (i).

FIG. 18 is a table showing the 3D data processing time of sub spectral bands and sub sampling band.

FIGS. 21A-21L show the calculated surface data. (a)-(l) are the cross sectional images at 0.5 mm, 1.0 mm, 1.5 mm, 2.0 mm, 2.5 mm, 3.0 mm, 3.5 mm, 4.0 mm, 4.5 mm, 5.0 mm, 5.5 mm and 6.0 mm, where the red curves are the estimated surface.

FIGS. 25A-25V show results of texture noise removing on a healthy volunteers palm data. (a) The photography of palm and the marked region was scanned. (b)-(d) are the en face structural images at three depth obtained by AGOCTA (mean value of the averaged two absolute Gabor filtered fringes). (e)-(g) and (n)-(p) are obtained by regular AGOCTA and SVOCT within three depth ranges. (h)-(j) and (q)-(s) are obtained by AGOCTA and SVOCT with texture noise removed. (k)-(m) and (t)-(v) are the differential images of optimized images and regular images for AGOCTA and SVOCT. All images share the same scale bar.

FIGS. 26A-26J show microvascular images on a HHT patient's skin lesion. (a) Photography of the lesion, where the marked region (6×6 mm) was scanned. (b) The estimated surface curvature. (c) The mask for dynamic blood flow signals and background on a local region marked by a dashed yellow rectangle in (f)-(h). (d) The en face structural image obtained by AGOCTA. (e)-(f) The en face microvascular images (at depth range of 650 to 950 µm below skin surface) obtained by regular SVOCT and AGOCTA, respectively. (g) Microvascular image obtained by cmOCT with correlation window of 3×3 pixels. (h)-(i) are obtained by SVOCT and AGOCTA with texture noise removed. (j)-(l) are histograms of the intensity values covered by mask (c), where dynamic and static signals were marked as red and blue, respectively. (d)-(h) share the same scale bar.

FIG. 27 plots 3D data processing time of sub spectral bands and sub sampling band.

FIGS. 28A-28M show microvascular images of AGOCTA on sub spectral and sub sampling bands. (a)-(l) are en face images with different spectral bands and different sampling bands. (a1)-(l1) are the zoomed local images in the marked region by a dashed rectangle in (a)-(l). (a2)-(l2) are the histograms of the pixel intensities in (a1)-(l1) covered by mask (m), where red and blue represent dynamic and static signals, respectively. (a)-(l) share the same scale bar.

FIGS. 29A-29J show microvascular images of the scalp of a healthy volunteer. (a) A photograph of the scalp, where the marked local region (6×6 mm$^2$) was scanned. (b)-(d) are the structural images within three different depth ranges. (e)-(j) are the microvascular images obtained by AGOCTA within three different depth ranges and the fringes of ½ spectral band and ½ sampling band are used. However, (e)-(g) and (h)-(j) are without and with texture artifact removing. (b)-(j) share the same scale bar.

FIGS. 30A-30I show images obtained using different example implementations of the GOCTA algorithm in the example case of retinal imaging. As can be seen in the figures, the image quality is maintained when using the "skipped convolution" method and/or the spectral-sub band method.

DETAILED DESCRIPTION

Figure 1A:
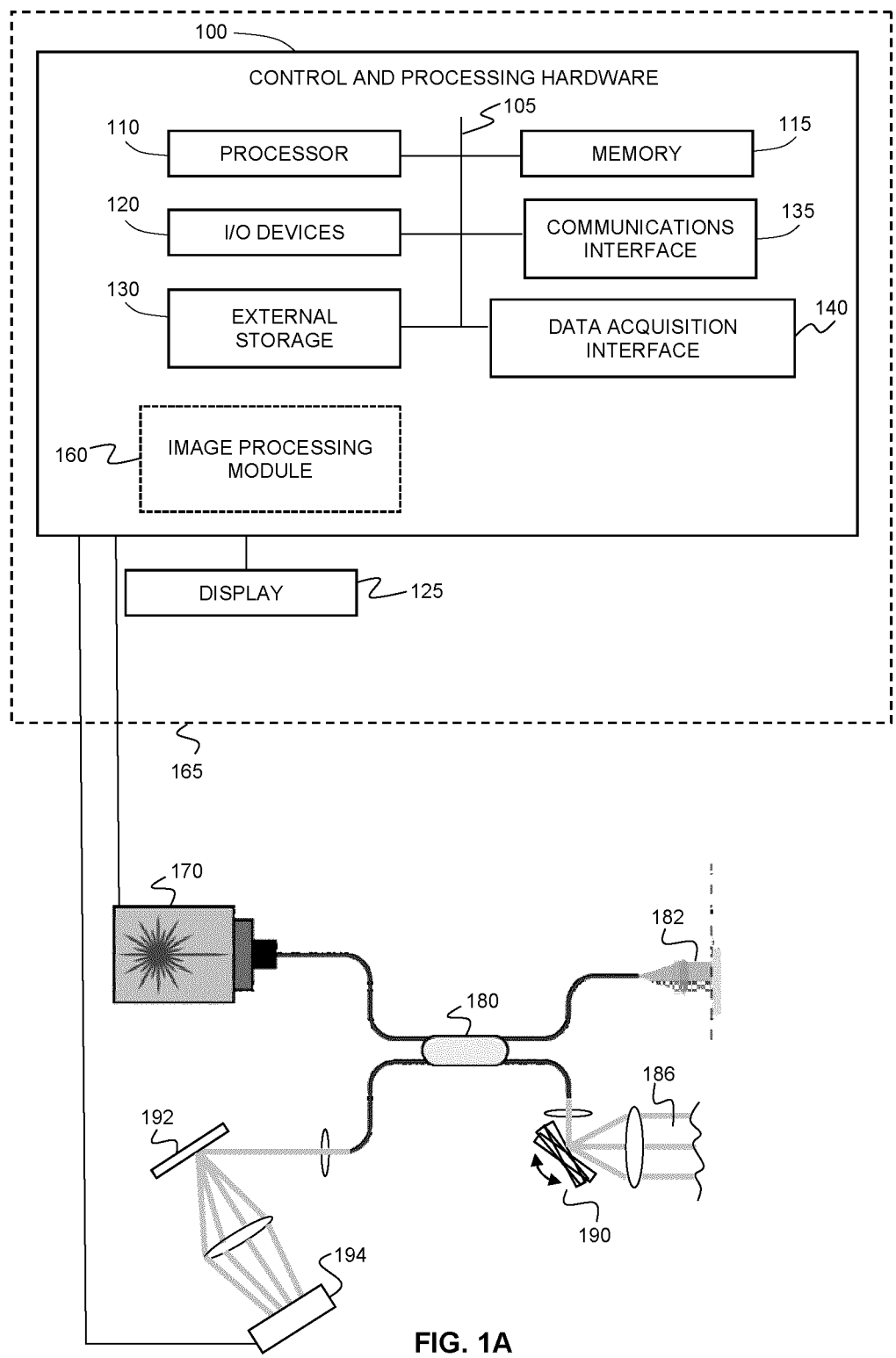
FIG. 1A shows an example system for performing optical coherence tomography angiography using spectral domain OCT (SDOCT).

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

In the various conventional OCTA methods described above, the blood flow information is obtained from the spatial domain. However, in order to reconstruct en face images, which appear to be the most useful display mode for clinical use, the SDOCT systems described above all require numerous complex processing steps, including k-space resampling, dispersion compensation, Fourier transform (FFT), and maximum (or mean) projection (MIP). Some of these processing steps require long processing times, which poses challenges for real-time imaging, even when using GPUs for data processing.

For clinical applications such as retinal imaging, the present inventors have recognized that OCTA images are typically used as en face image sets for clinical decision making, such as identifying an area of microvascular abnormality, after which depth resolved information, such as cross-sectional structural OCT images of the retina at the particular region, are reviewed. Therefore, rapid en face OCTA image display, at the time of scanning, may be advantageous to screen retinal pathology as well as to focus detailed examination on a smaller region of interest. In such scenarios, rapid en face OCTA may allow immediate feedback and re-scanning. Such capability may also be useful for less cooperative patients where motion artefacts degrade OCTA images. The present inventors thus sought out to improve upon current OCTA detection and processing methods in order to develop a rapid OCTA method that would enhance the clinical utility of real-time OCTA imaging and video display.

The present inventors also recognized that while most existing OCTA algorithms carry out many computationally intensive steps during depth-resolved image processing, in the last steps of the algorithms, an intensity projection is performed in the depth direction—thereby discarding the depth information that had been generated through the computationally intensive processing steps. In contrast, in various example embodiments of the present disclosure, optical coherence tomographic angiography OCTA algorithms are provided in which blood flow information is directly extracted from interference fringes without performing the time-consuming steps mentioned above, thereby facilitating real-time OCTA video display. As shown in the Examples provided below, the various example implementations of the methods disclosed herein have been shown to significantly decrease data processing time while maintaining image quality that is suitable for real-time clinical applications.

Referring now to FIG. 1A, an example system is shown for performing OCTA based on spectral domain OCT (SDOCT). The system includes, but is not limited to, a broadband source 170, a line array detector 194, a beamsplitter 180, a sample arm 182, a reference arm 186, and a spectrally dispersive optic 192. The system may include one or more scanning devices (e.g. motor controlled galvo mirrors), shown at 190, for scanning the beam of the sample arm relative to an object (e.g. tissue).

The beamsplitter 180 splits light from the broadband source 170 between the reference arm 184 and the sample arm 186 and the light reflected from the two arms is interfered. In the example embodiment shown in the figure, in which an example fiber-optic based implementation is shown, the reflected light is interfered using the beamsplitter 180. In other example implementations (such as, for example, free-space optical implementations), a different beamsplitter may be employed. The interfered light is dispersed using the dispersive optic 192, which may be a dispersion grating. The dispersion optic 192 spatially disperses the different spectral components of the interfered light, and the spatially dispersed spectrum is detected using the photodetector array 194 (e.g. a line camera). As will be understood by those skilled in the art of optical coherence tomography, the detected spectrum is the Fourier transform of the axial scan line (A-line), thereby encoding the reflectivity of the tissue as a function of depth.

The broadband source 172, detector array 194, and scanning system are operatively coupled to control and processing hardware 100. As shown in the example embodiment illustrated in FIG. 1A, the control and processing hardware 100 may include a processor 110, a memory 115, a system bus 105, one or more input/output devices 120, and a plurality of optional additional devices such as communications interface 135, display 125, external storage 130, and data acquisition interface 140. In one example implementation, the display 125 may be employed to provide a user interface for displaying en face OCTA video and/or images, and/or for providing input to control the operation of the system. As shown in FIG. 1A, the display may be directly integrated into a control and processing device 165 (for example, as an embedded display), or may be provided as an external device (for example, an external monitor).

The methods described herebelow can be implemented via processor 110 and/or memory 115. As shown in FIG. 1A, executable instructions represented as image processing module 160 are processed by control and processing hardware 100 to generate en face OCTA images and/or video as per the example methods described below. The control and processing hardware 100 may include, for example, and execute instructions for performing one or more of the methods illustrated in FIG. 2 and/or FIGS. 7A and 7B, or other methods described herein, or variants thereof. Such executable instructions may be stored, for example, in the memory 115 and/or other internal storage. Additional control modules may be provided, for example, for controlling the scanning operations of one or more scanning mirrors (e.g. galvo controllers).

The methods described herein can be partially implemented via hardware logic in processor 110 and partially using the instructions stored in memory 115. Some embodiments may be implemented using processor 110 without additional instructions stored in memory 115. Some embodiments are implemented using the instructions stored in memory 115 for execution by one or more microprocessors. Thus, the disclosure is not limited to a specific configuration of hardware and/or software.

It is to be understood that the example system shown in the figure is not intended to be limited to the components that may be employed in a given implementation. For example, the system may include one or more additional processors. Furthermore, one or more components of control and processing hardware 100 may be provided as an external component that is interfaced to a processing device. Furthermore, although the bus 105 is depicted as a single connection between all of the components, it will be appreciated that the bus 105 may represent one or more circuits, devices or communication channels which link two or more of the components. For example, the bus 105 may include a motherboard. The control and processing hardware 100 may include many more or less components than those shown.

Some aspects of the present disclosure can be embodied, at least in part, in software, which, when executed on a computing system, transforms an otherwise generic computing system into a specialty-purpose computing system that is capable of performing the methods disclosed herein, or variations thereof. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine-readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

Figure 1B:
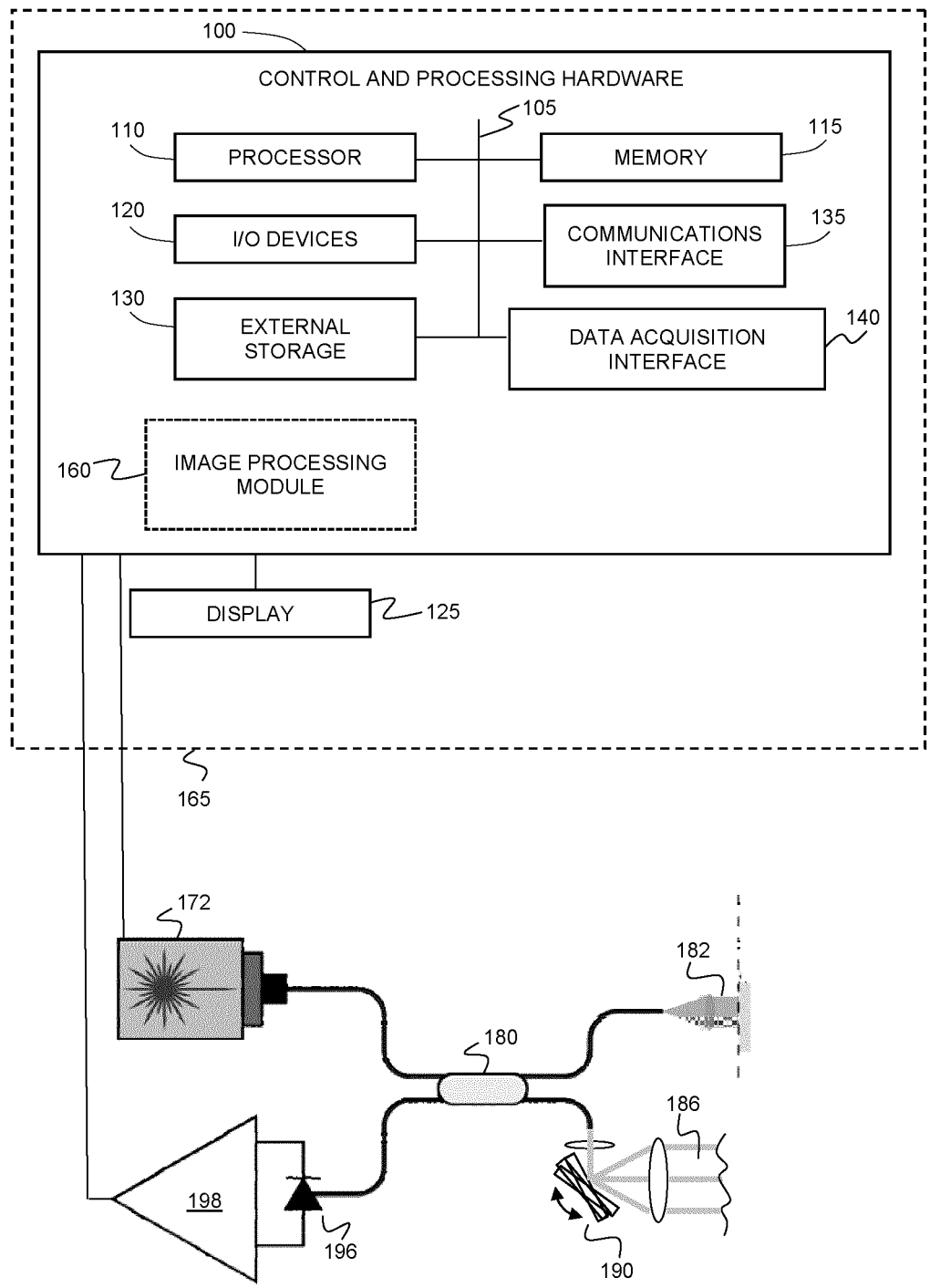
FIG. 1B shows an example system for performing optical coherence tomography angiography using swept-source OCT (SSOCT).

FIG. 1B illustrates an alternative example implementation of a system for performing OCTA based on swept source OCT (SSOCT). The example system includes a swept-source optical coherence tomography system, that includes, but is not limited to, a tunable laser 172, a detector 196, an amplifier 198, a beamsplitter 180, a sample arm 182, and a reference arm 186. The system may include one or more scanning devices (e.g. motor controlled galvo mirrors), shown at 190, for scanning the beam of the sample arm relative to an object (e.g. tissue). It will be understood that the tunable laser employed for such an implementation may be an akinetic laser in order to improve image quality.

The tunable laser 172 is employed to tune or "sweep" the optical wavelength of light emanating from the laser, and the resulting interference pattern, corresponding to a wavelength sweep of the tunable laser, is detected as time-dependent signal for each A-line. Spectral analysis (via a Fourier transform) of the detected signal can be employed to generate a depth profile of the reflectivity of the sample. One or more additional control modules may be provided for synchronizing operation of a tunable laser 172 with the scanning operations.

Figure 2:
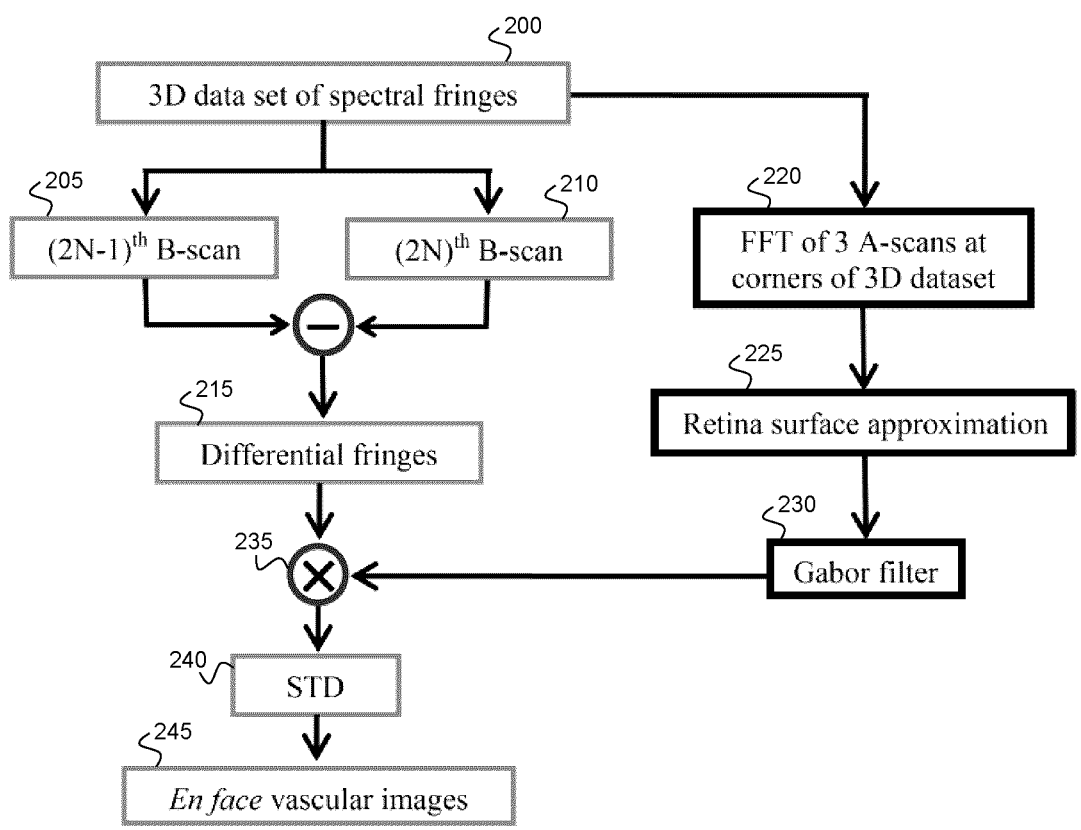
FIG. 2 shows a flow chart illustrating an example method of performing Gabor optical coherence tomographic angiography (GOCTA). The right side of the flow chart shows an example method of calculating the surface depth of the imaged tissue surface, in which three A-scans are initially calculated to determine the approximate retinal surface location, thereby providing Gabor filter parameters for the B-scan processing that is performed on the left side of the flow chart.

Referring now to FIG. 2, an example method of performing OCTA for the rapid generation of en face images and/or video is illustrated. The example method shown in this figure is referred to as Gabor-OCTA, or GOCTA, in the present disclosure. In one example implementation that employs SDOCT, the interference fringes between the light backscattered from sample and reflected by the reference mirror are detected by a spectrometer camera. A three-dimensional (3D) dataset of spectral interferogram frames (spectral fringes), collected as shown at 200 is acquired (e.g. scanning using x- and y-galvo-mirrors). The direct component (DC) of the interference (auto-correlation of reference beam) can be measured by blocking sample arm and the auto-correlation of sample beam is negligible.

After subtracting the DC component, the captured signal can be simplified by $$I(x, \lambda, y) = S(\lambda) \int_{-\infty}^{\infty} \sqrt{R_{(x,z,y)} R_r \gamma_s \gamma_r} \cos\left(\frac{4\pi}{\lambda} nz + \phi_{(x,y)} + \phi_{dis}(\lambda)\right) dz, \qquad (1)$$

where x and y represent the scanning directions (e.g. of the two galvos), $\lambda$ is wavelength, $S(\lambda)$ is the power spectral density of light source, $R_{(x,y,z)}$ and $R_r$ are the backscattering coefficient of sample and the reflectivity reference mirror, respectively. $\gamma_s$ and $\gamma_r$ are the input power in the sample and reference arms, n is the refractive index, z represents depth, $\phi_{(x,y)}$ and $\phi_{dis}(\lambda)$ are the initial phase and the dispersion mismatch between sample arm and reference arm.

In the case of moving particles, the amplitude and the frequency of the fringes vary with time. However, for two consecutive B-scans acquired from the same position, acquired as shown at steps 205 and 210, the amplitude or frequency of the components corresponding to moving particles is different. Subtracting the two B-scans, the components corresponding to static tissue can be removed, and the resultant signal originates from the moving particles. The differential spectral interferogram frame, shown at 215 in FIG. 2, can be expressed by $$I'(x,\lambda,y) = I(x,\lambda,y_1) - I(x,\lambda,y_2), \qquad (2)$$

where $I(x,\lambda,y_1)$ and $I(x,\lambda,y_2)$ are two consecutive B-scans from the same position.

Figure 3:
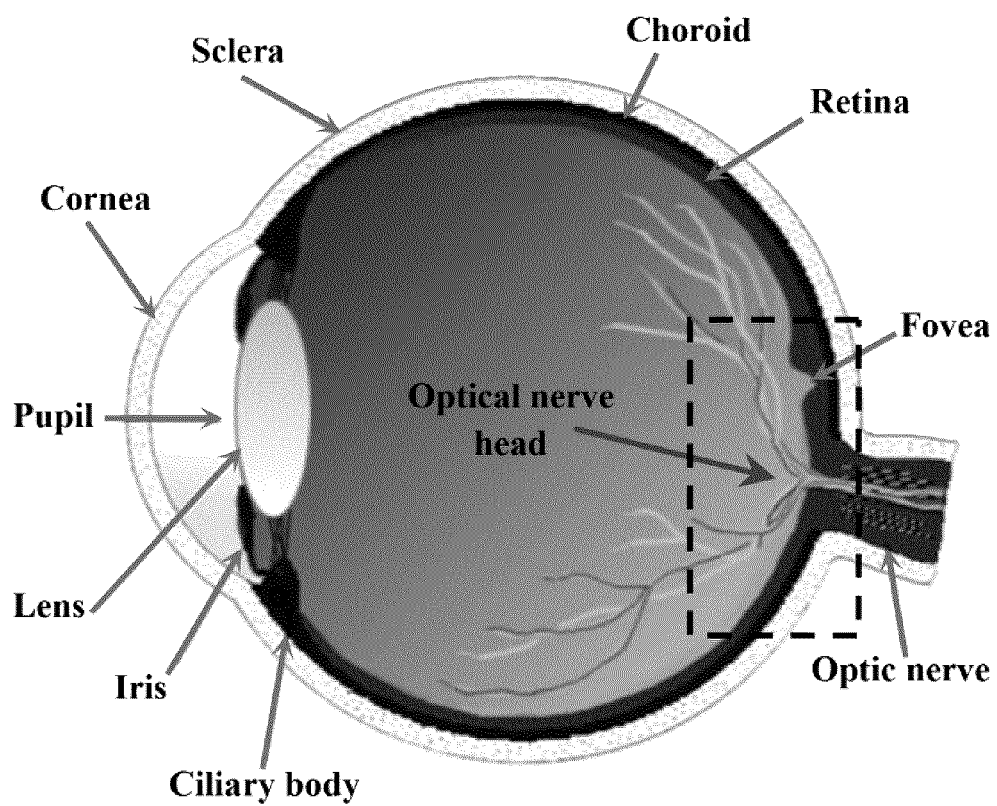
FIG. 3 is a cross-sectional structural diagram of the human eye. In some example embodiments, the curvature of the retinal surface within the region covered by the dashed box can be approximated by the anterio-posterior (AP) diameter.

As shown in FIG. 3, the human eye, as an optical system, has a curved image plane on the retina near the fovea, with the optical nerve head in the vicinity. The anterio-posterior (AP) diameter of an emmetropic human adult eye is approximately 22 to 24 mm, which is relatively invariant between sex and age groups. While the transverse diameter varies more according to the width of the orbit, the curvature of the area near the fovea and optical nerve head can be approximated by the AP diameter. Accordingly, in some example embodiments of the present disclosure, an AP diameter within the range of 21-23 mm or 21.5 to 22.5 mm (or radius of curvature of within the range of 10.5 to 11.5 mm, or 10.75 to 11.25 mm) may be employed as an approximation for human eyes.

According to the example GOCTA method shown in FIG. 2, the orientation of retina is determined for the subsequent generation of Gabor filters having depth selectivity corresponding to the tissue surface depth. In one example implementation, the retinal orientation may be evaluated based on a spherical model which can be expressed as:

$$(x-x_0)^2(y-y_0)^2+(z_s-z_0)^2=R^2, \quad (3)$$

where $(x_0, y_0, z_0)$ and R are the center position and the radius, respectively, $z_s$ is the depth of retinal surface in structural images.

In the present example method, in order to calculate the center location $(x_0, y_0, z_0)$, at least three surface points $(x, y, z_s)$ are needed. In one example implementation, the surface points FFT may be determined by processing at least three A-scans (e.g. at corners of the image frame) to determine the depth of surface, as shown at 220 in FIG. 2. The retinal surface $z_s(x, y)$ can be then determined by fitting the surface points to using eq. 3, thereby approximating the region marked by the dashed box in FIG. 3, as per step 225 of FIG. 2.

It is noted that since the human retinal surface curvature can be complex, the accuracy of the estimated surface data can be improved by using a distributed set of A-scans (e.g. evenly distributed among across the tissue surface of interest), and 2D cubic interpolating the surface positions of the A scans. This method provides a more accurate surface depth estimation than the preceding example method that employed 3 corner surface positions to solve a sphere function.

Within the measured interference fringes, the sample information at different depths is modulated by different frequency components. As a Gabor filter is a linear filter, the frequency component within a specific frequency range can be obtained directly by convolution, which is equivalent to multiplying a Gaussian function in spatial domain. For example, the Gaussian function $g(z)=\exp[-4 \ln 2(z-\delta z)^2/\Delta z^2]$ can be used to extract the sample information within the depth range of $\delta z-\Delta z/2$ to $\delta z+\Delta z/2$, where $\delta z$ and $\Delta z$ are the depth and depth range respectively. Taking the refractive index and round optical path into account, the filter can be obtained by performing a FFT on the above mentioned Gaussian function and expressed by $$G(x, k, y) = \exp\left[-\frac{\pi^2(n \cdot \Delta z)^2(k-k_0)^2}{\ln 2}\right]\cos[2\pi(k-k_0)(z_s(x, y)+2n\cdot\delta z)+\varphi_0], \quad (4)$$

where k and $k_0$ are wavenumber and center wavenumber, $\varphi_0$ is the initial phase. The Gabor filter based on wavelength $G(x,\lambda,y)$ is then calculated by performing a reverse resampling on $G(x,k,y)$. This step of calculating the Gabor fitter, based on the approximate retinal surface at the pixels of the differential interferogram image frame, is shown at step 230 of FIG. 2. By changing the values of $\Delta z$ and $\delta z$, the en face microvascular images at different depths and within different depth ranges can be obtained.

By performing convolution on the differential spectral interferogram frame with Gabor filter, a new differential frame is obtained, henceforth referred to as a Gabor-convolved differential spectral interferogram frame. This step is shown at step 235 in FIG. 2, and is computed as:

$$I''(x,\lambda,y)=I'(x,\lambda,y)\otimes G(x,\lambda,y), \quad (5)$$

The GOCTA signal can then be obtained by calculating the standard deviation (STD) of the Gabor-convolved differential spectral interferogram frame $I''(x,\lambda,y)$, as shown at step 240, which is expressed by:

$$GOCTA(x, y) = \sqrt{\frac{1}{M}\sum_{n=1}^{M}[I''(x, \lambda_n, y) - I''_{mean}(x, y)]^2}, \quad (6)$$

where M is the pixel number of CCD, $I''_{mean}(x,y)$ is the mean value of each A-scan of the filtered fringe. By calculating GOCTA signal for each position in the 3D dataset of spectral fringes, en face microvascular images can be directly obtained.

It will be understood that the although many of the example embodiments disclosed herein involve the generation of the en face signal by computing the standard deviation of the Gabor-convolved differential interferograms, the standard deviation is but one example of many operations that may be employed to generate the en face image.

Accordingly, in some example implementations, a given pixel of the en face angiography image is generated by calculating, for a respective pixel of the Gabor-convolved differential spectral interferogram frame, measure based on a spectral standard deviation. In other example, embodiments, a given pixel of the en face angiography image is generated by calculating, for a respective pixel of the Gabor-convolved differential spectral interferogram frame, a measure quantifying a spectral statistical dispersion. Non-limiting examples of statistical measures include median absolute deviation and average absolute deviation. In some example implementations, the measures of variance may be higher order power/roots of variance, or combination thereof.

In the present example embodiment, the Gabor filter parameters may be chosen such that a large number of zeros are encountered, thus simplifying the computational complexity and reducing the time needed for the convolution in digital filtering. For example, it was found that microvascular images within a depth range of 350 μm (10% of the total OCT ranging depth in one example implementation in the Examples below) spherically fitted retinal surface may be calculated for analysis and comparison. In this example implementation, the non-zero segment length of Gabor filter (Eq. 4) was found to be only 16 pixels (see the Example section below for details of the example system employed), resulting in a substantial decrease of computation complexity.

As can be readily appreciated from FIG. 2, the example GOCTA methods disclosed herein avoid the step of calculating depth resolved structural images (in the z-direction), in contrast to the conventional methods described above. Accordingly, the present systems and methods may be potentially useful for calculating the preview OCTA images as the first line en face display for the clinician, and improve the efficiency of disease screening and diagnosis in busy clinical environment.

As shown in the Examples below, the GOCTA method, and variations thereof, may result in significantly reduced image processing times relative to the conventional methods. Indeed, by obviating the need of resampling, dispersion compensation and FFT, the present example processing methods have been shown to achieve a 6, 4 and 20 times of the data processing speed compared to SVOCT, UHS-OMAG and SSADA, respectively.

In some example implementations, the Gabor optical coherence tomographic angiography (GOCTA) methods disclosed herein may be employed to provide images and/or video of the microvasculature of a human retina using a standard ophthalmic SDOCT system. The present GOCTA methods are well suited for SDOCT systems used in wide field scanning, ultra-high spectral resolution or parallel high A-line speed applications, where large data amount is generated. In order to improve processing times for real-time imaging, the present GOCTA methods can also be implemented on graphics processing units (GPUs) to increase data processing speed further.

Although the preceding description of the GOCTA method was provided with reference to implementation using an SDOCT system, it will be understood that the preceding example embodiments may alternatively be implemented using a SSOCT system. As noted above, such a system is illustrated in FIG. 1B. It will be understood that the tunable laser employed for such an implementation may be an akinetic laser in order to improve image quality.

It is noted that a limitation of the example GOCTA method illustrated in FIG. 2 is that the structural image alignment in the z-direction cannot be performed for motion artefact removal. However, it is nonetheless noted that x- and y-direction based en face image registration and alignment may still be applied. In clinical use, the GOCTA method can be employed to provide en face images and/or video (e.g. preview images or video), and subsequent processing of the 3D interferogram dataset may optionally be employed to extract depth profile information.

While the curvature of the lens system can affect the accuracy of the evaluated retinal orientation, and for slight curvature, the images obtained by the GOCTA method will not be affected due to the depth range of Gabor filter being a small fraction (e.g. approximately 10%) of the total OCT ranging depth. In the case of significant curvature, the relative shifting distance at each pixel can be obtained by scanning a mirror and the evaluated retinal orientation can be compensated in software.

As noted above, in some example embodiments, the surface calculation method shown in steps 220 and 225 of FIG. 2, and the resulting accuracy of the surface data, can be improved compared to that used in the aforementioned method. FIGS. 4A-4C illustrate an example implementation for achieving improved surface data and accuracy. As shown in FIGS. 4A-4C, after the 3D dataset of spectral fringes (FIG. 4A) was acquired, a FFT was performed on a set of (approximately) uniformly distributed A-scans (e.g. 9×9 or less, or 30 A scans or less, or 100 A scans or less) in order to calculate the surface information of tissue, and the result is shown in FIG. 4B. 2D cubic interpolation was then performed on the surface data to estimate the entire surface of sample, as shown in FIG. 4C. It is noted that the number of uniformly distributed A-scans could be increased to further improve the accurate of surface data in the case of more complex surface curvature. It will be understood that the surface depth characterization of the tissue surface may be performed using another modality, such as, but not limited to, a surface profile detection system (e.g. using structured light).

In the example GOCTA method described above, since the moving scatters can change the frequency or amplitude of the spectral fringes obtained by OCT, the standard deviation of the Gabor-convolved differential fringes of the two B-scans from the same position was selected as the GOCTA signal to contrast microvasculature. However, it has been found by the inventors that, for human eye imaging, the backscattered intensity can be modulated by the retinal texture pattern, resulting in a decrease of sensitivity for extracting vascular information. As a result, some vascular information in the local regions with a weak backscattered intensity may be lost.

To address this problem, the STD of differential fringes was divided by the total energy of the two A-scans, and the resulting improved GOCTA signal can be expressed by:

$$GOCTA = \sqrt{\frac{\sum_{n=1}^{M}[Id'(\lambda_n) - Id'_{mean}]^2}{\sum_{n=1}^{M} I_1(\lambda_n)^2}}, \quad (1)$$

where x and y are the pixel index for fast scanning and slow scanning directions, respectively. $DI(x,\lambda,y_1)$ and $DI(x,\lambda,y_2)$ are the two B-scans obtained by SDOCT from the same position, $\lambda$ is wavelength, $DI''$ is the Gabor filtered differential fringes of the two frames from same position. As noted above, the standard deviation calculation in the equation above may alternatively be computed as one or many different measures of spectral statistical dispersion, optionally including a higher order power or root or combination thereof.

It is further noted that since the spectral density function of the laser in SDOCT is a Gaussian function, whereby the center portion of the spectrum carries the majority of the sample information due to the stronger intensity. Accordingly, in some example embodiments, the spectral fringes obtained by the OCT system could be shortened in bandwidth, in order to decrease computation complexity, without significantly degrading image quality, thereby achieving a higher data processing speed. Furthermore, while the standard deviation of the differential fringes over the total energy of the two fringes was used for contrasting microvasculature in GOCTA, each pixel carried the information of moving scatters, and as a result, the spectral fringes could also be spectrally sub sampled to further improve data processing speed.

FIGS. 5A-B schematically illustrate example methods of performing sub spectral band sampling, and sub sampling within a spectral band ("sub sampling band"). In FIG. 5A, a spectral subset of the differential interferogram is processed. For example, according to various non-limiting example embodiments, the spectral subset of the differential interferogram may be a quarter or a half of the full band. FIG. 5B illustrates the sub-sampling of the differential interferogram, illustrating non-limiting cases in which one of every two spectral pixels are sampled, and one of every three spectral pixels is sampled. It is noted that in the case of sub spectral band sampling shown in FIG. 5A, the Gabor filters did not need to be shortened. However, in the example embodiment shown in FIG. 5B, both the interferogram and the Gabor filters are sub sampled, since the spectral resolution is changed by this method.

In the case of performing a conventional convolution, each pixel is used $N_g$ times during the calculation of the convolution (where $N_g$ is the size of the Gabor filter kernel). However, as repeated use of each pixel does not provide additional differential information for GOCTA signals, the convolution method may be adapted to reduce the number of times a pixel is employed during the convolution to further decrease computing amount for data processing. The conventional method of performing the convolution involves the shifting of the Gabor filter by one pixel between successive steps of the convolution. In contrast, in some example embodiments, the Gabor filter may be shifted by a plurality of pixels that is less than the kernel of the Gabor filter between successive steps (e.g. between at least one successive step) when performing the convolution, such that $n<N_g-1$ pixels of the spectral interferogram are skipped between steps of the convolution.

FIG. 5C illustrates one example and non-limiting implementation of such a "skipped convolution" method, in which the Gabor filter is shifted by $N_g$ pixels for each step during the convolution process (skipping $N_g-1$ intermediate convolution steps), such that each pixel is employed only once during the convolution. When compared to methods employing a conventional convolution, this present example implementation can significantly increase the image processing speed without compromising image quality. As shown in FIGS. 30A-30I in the example provided below, the skipped convolution method may be combined with the preceding sub-spectral band methods.

In some example embodiments, the preceding example GOCTA methods are adapted according to a method involving the convolution of Gabor filters with two interferograms, and the subsequent subtraction of the amplitudes of the Gabor-convolved interferograms. This modified OCTA method is henceforth termed amplitude based Gabor OCTA (AGOCTA). This method may be beneficially applied to SSOCT systems, where the processing method may reduce and/or reject the timing-induced phase errors caused by swept source lasers, while achieving reconstructed en face microvascular images with a faster data processing speed compared to the two popular skin imaging algorithms (cm OCT and SVOCT) that are commonly used for SSOCT systems.

FIG. 7A provides a flow chart illustrating example implementations of the example AGOCTA method. A 3D data-set of spectral interferogram frames (spectral fringes) is acquired (e.g. using a SSOCT system), as shown at step 300 and each position is scanned at least twice, thereby providing interferogram frames as shown at 305 and 310. According to Choma et al. (Choma, R. et al., Opt. Exp. 11, 2183 (2003)), the obtained spectral interferogram frames could be expressed by $$I(k)=S(k)\int_{-\infty}^{\infty}\sqrt{R_s R_r \gamma_s \gamma_r}\cos(kz+\phi_0)d_z, \quad (1)$$

where k is wavenumber, S(k) is the power spectral density of the light source, $R_s$ and $R_r$ are the scattering coefficient of sample and the reflectivity reference mirror, respectively. $\gamma_s$ and $\gamma_r$ are the input power in the sample and reference arms, respectively. $\phi_0$ is the initial phase.

As in the preceding example GOCTA method, the frequency components within specific depth range in spatial domain may be obtained by convolving with Gabor filters in which surface data was needed.

Referring again to FIGS. 4A-4C, in order to estimate the surface of tissue, an FFT may be performed on a subset of (e.g. 5×5) of A-scans that are (approximately) uniformly distributed on an xy plane, in order to calculate surface positions. Subsequently the overall surface may be estimated by 2D cubic interpolating the matrix of surface positions. This calculation is shown at step 315 of FIG. 7A. In the case of tissue, which has a more complex surface curvature than the retinal surface considered above, a higher density of A-scans may be useful to obtain a more accurate calculation of the surface profile. It will therefore be apparent that there is a trade-off between the computational complexity required for surface profile (depth) characterization and overall processing time.

Having obtained the surface information, the Gabor filters can be obtained, as shown at 320, and may be expressed by:

$$G(k)=\exp\left[-\frac{\pi^2(n\cdot\Delta z)^2(k-k_0)^2}{\ln 2}\right]\cos[2\pi(k-k_0)(z_s+2n\cdot\delta z)+\varphi_0], \quad (2)$$

where $k_0$ is central wavenumber, $z_s$ is the surface position, $\Delta z$ is the depth range, n is the sample's refractive index, $\delta z$ represents the depth of filter below the surface and $\varphi_0$ is the initial phase.

Blood flow signals may then be calculated by convolving the two interferogram frames from the same position with the Gabor filters, with the sub-band fringes corresponding to the specific depth range, as shown at 325 and 330:

$$I'(k)=I(k)\otimes G(k), \quad (3)$$

where $\otimes$ is the operator of convolution.

A Hilbert transform and amplitude operation are then performed on the Gabor-convolved spectral interferogram frames, as shown at 335, 340, 345 and 350 in order to calculate the amplitude plots of the two frames. By subtracting the amplitude plots of the two frames, as shown at 355, the differential Gabor-convolved spectral interferogram amplitude frame is obtained and expressed by:

$$I''(k)=\text{Amp}[\text{Hilbert}(I'_{2N-1}(k))]-\text{Amp}[\text{Hilbert}(I'_{2N}(k))], \quad (4)$$

where Amp and Hilbert are amplitude operator and Hilbert transform. Lastly, the standard deviation of the differential Gabor-convolved spectral interferogram amplitude frame is calculated, in order to contrast blood flow signals, as shown at 360, and as follows:

$$AGOCTA=\sqrt{\frac{1}{M}\sum_{n=1}^{M}[I''(k_n)-I''_{mean}]^2}, \quad (5)$$

where M is the pixel index in each A-scan, $I''_{mean}$ is the mean value of the fringes. By calculating the STD of each A-scan within the 3D dataset of spectral fringes, the en face microvascular images are obtained.

It will be understood that the although many of the example embodiments disclosed herein involve the generation of the en face signal by computing the standard deviation of the differential Gabor-convolved spectral interferogram amplitude frame, the standard deviation is but one example of many operations that may be employed to generate the en face image.

Accordingly, in some example implementations, a given pixel of the en face angiography image is generated by calculating, for a respective pixel of the differential Gabor-convolved spectral interferogram amplitude frame, measure based on a spectral standard deviation. In other example, embodiments, a given pixel of the en face angiography image is generated by calculating, for a respective pixel of the differential Gabor-convolved spectral interferogram amplitude frame, a measure quantifying a spectral statistical dispersion.

Non-limiting examples of statistical measures include median absolute deviation and average absolute deviation. In some example implementations, the measures of variance may be higher order power/roots of variance, or combination thereof.

As noted above in the context of the GOCTA method, the backscattering intensity may be modulated by the texture pattern of the imaged tissue. For example, texture pattern modulation may occur for tissues such as such as finger and palm print, lesion, etc., as shown in FIG. 6A.

For skin imaging, it is inevitable that the height of skin surface 500 (finger and palm print) or skin's scattering coefficient (skin lesion) changes sharply, resulting in modulated backscattered intensities by skin texture pattern for the same vessel 505, as shown in FIGS. 6A and 6B. By using the modulated intensities to calculate blood flow signals, the obtained microvascular images are also modulated by the texture patterns, appeared as discontinuity of vessels.

For example, referring to FIG. 6A, assuming the backscattered intensities by red blood cells (RBC, 510) at position 1 and position 2 are $I_1$ and $I_2$, respectively, $I_1$ will be stronger than $I_2$, since the depth of RBC at position 1 is smaller than position 2. In capillaries, RBCs move in a single file, with variable distances in between, and therefore, it is possible after the time required for a complete B-scan, there can be an "all or none" phenomenon since certain locations will have backscatter signal from a RBC while other locations will have none. Considering the SVOCT method as an example, the STDs obtained at the two positions for the same vessel are $I_1/2$ and $I_2/2$ ($I_1>I_2$), respectively, resulting in discontinuity of vessels. Accordingly, microvascular images obtained using the modulated intensity signals are also modulated by skin texture pattern, appearing as a discontinuity of vessels. As shown in FIG. 6B, in patients having skin lesions 515, especially with increased scattering or absorption coefficients, the lesions 515 may impose a strong texture effect on the angiographic image processing, again causing discontinuity of vessels.

In one example embodiment, the aforementioned AGOCTA method may be adapted to reduce texture modulation effects as follows. Referring again to FIG. 7A, by dividing the obtained AGOCTA image by the mean value of the averaged fringes of the two absolute Gabor filtered fringes, as shown at steps 365, 370, 375 and 380, a new AGOCTA image is obtained where the texture pattern is reversed. The en face images with texture noise removal or reduction may then be obtained by summing the normalized new AGOCTA image and normalized log scale of original AGOCTA image, as shown at steps 385, 390, 392, 394, 396 and 398, which is expressed by $$AGOCTA' = Norm\left(\frac{AGOCTA}{\sum_k [\text{abs}(I'_{2N-1}(k)) + \text{abs}(I'_{2N}(k))]}\right) + Norm(\log(AGOCTA)) \quad (6)$$

where Norm (392, 394) and Abs (365, 370) are the normalize and absolute operator, respectively.

In the Examples provided below, the aforementioned method of suppressing texture noise is demonstrated on a healthy volunteers palm and a hereditary hemorrhagic telangiectasia (HHT) patient's skin lesion.

The preceding texture noise suppression method may also be employed for SVOCT imaging, as shown in FIG. 7B. In the method shown in FIG. 7B, which is a modification of the SVOCT method, after structural images were obtained by FFT, the same MIP window was performed on both STD images and averaged structural images, as shown at 400 and 405, in order to calculate original en face SVOCT images and en face structural images. By dividing SVOCT image by structural images, as shown at 410, a new SVOCTA image is obtained with texture pattern reversed as well. As in the preceding AGOCTA texture noise reduction method, the final SVOCTA images with texture noise suppression are obtained by summing the normalized new SVOCT image and normalized log scale of original AGOCTA image, as shown at steps 415, 420, 425, 430 and 435.

In the Examples section below, the example AGOCTA method described above has been shown to provide faster data processing speed in comparison to other two SSOCT blood flow imaging algorithms, SVOCT and cmOCT, that are performed in the spatial domain. This advantage is understood to be mainly due to calculation of the blood flow signal from the spectral domain directly, which can decrease the computationally intensive processing time. One limitation of the AGOCTA method is the lack of depth resolved information. However, since most clinicians are more familiar with en face microvascular images, such limitations may not be detrimental. For example, as in the case of the GOCTA method described above, the AGOCTA method may be used for calculating preview images and/or video in order to improve the diagnosing efficiency for the doctors in clinics. This workflow may be beneficial, for example, in the case of uncooperative patients.

Compared to the example GOCTA method described above, the data processing time for the present example AGOCTA method was found to almost double because the convolution of Gabor filter was performed on the differential spectral fringes of the two A-scans from the same position in GOCTA, while in AGOCTA, the convolution was separately performed on the two A-scans and then the differential amplitude plots of the two filtered fringes were used for STD calculation.

Although the preceding description of the AGOCTA method was provided with reference to implementation using an SSOCT system, it will be understood that the preceding example embodiments may alternatively be implemented using a SDOCT system. As noted above, such a system is illustrated in FIG. 1B.

The experimental results shown in the Examples below demonstrate that the proposed methods can provide similar image quality (SNRs and CNRs) compared to the conventional OCTA algorithms that require significantly longer processing times. For cmOCT, SNR and CNR can be improved by increasing correlation window size, with heavy penalty on the data processing speed and lateral resolution.

Although many of the present example embodiments have been disclosed with reference to performing the present OCTA methods (GOCTA and AGOCTA) on the human retina and skin, it will be understood that these example embodiments are merely provided as example applications of the present methods. In other example embodiments, the present example embodiments may be employed to perform OCTA imaging on any tissue surface having vascularization associated therewith, such as, but not limited to, brain tissue, cardiac tissue, muscle, respiratory and gastrointenstinal tissue, abdominal organs such as bladder or ureter.

Clinical applications for the systems and methods disclosed herein include, but are not limited to, microvascular imaging, including but not limited to cortical neurovascular coupling assessment such as functional neuroimaging, monitoring of therapeutic effects on retinal pathology, assessment of microvasculature of organ transplant in terms of perfusion status, monitoring of angiogenesis in neoplastic and non-neoplastic disorders.

EXAMPLES

The following examples are presented to enable those skilled in the art to understand and to practice embodiments of the present disclosure. They should not be considered as a limitation on the scope of the disclosure, but merely as being illustrative and representative thereof.

Example: Use of GOCTA Method for Angiography of Eye

An example implementation of the aforementioned GOCTA method was performed on a dataset based on detection of a healthy human eye using a commercial SDOCT system (AngioVue, OptoVue Inc.) to verify its performance. This system operated at a center wavelength of 840 nm with the axial resolution and lateral resolution of ~5 μm and ~15 μm, respectively. The A-scan rate is 70,000 A-scans per second. In this example, the scanning range was 3×3 mm and each position was scanned twice.

Retinal OCT scanning was performed on ten healthy volunteers. Example data for two local regions (optical nerve head region and fovea region) are shown in FIGS. 8A-8O and 9A-9O, respectively. The scanning ranges were 3×3 mm with 608×304 A-scans. SVOCT, UHS-OMAG and SVOCT algorithms were performed on the same dataset to calculate microvascular images for comparison and the en face images were obtained by using mean projection within the depth range, same as the result obtained by Gabor filters. All of the en face microvascular images were calculated within depth of 0-350 μm below the retinal surface. Signal to noise ratio (SNR) and contrast to noise ratio (CNR) of the en face micro-vascular images were also calculated for quantitative comparison, SNR and CNR were calculated by $$SNR = \bar{I}_{dy}/\sigma_{bg}, \quad (7)$$

and $$CNR = (\bar{I}_{dy} - \bar{I}_{bg})/\sigma_{bg}, \quad (8)$$

where $\bar{I}_{dy}$ and $\bar{I}_{bg}$ represent the mean values within the dynamic flow region and background region, respectively, and $\sigma_{bg}$ is the standard deviation within the background region.

To quantitatively assess the microvascular and background signals for comparison, the marked regions were double-thresholded to obtain the masks for dynamic signals (red) and background (blue), as shown in FIG. 8C and FIG. 9C, which include vessels of different sizes. The results demonstrate that the GOCTA method can provide comparable image quality compared to the other three algorithms in the vicinity of both the optical nerve head and fovea regions, as shown by the comparable SNRs and CNRs. The output images from commercial SSADA algorithm use duplicated optical scanning in two directions (x and y) with post-processing applied on these two data sets to suppress motion artifact. The SNRs and CNRs were measured and calculated on all ten volunteers' data sets from healthy volunteers and the average and standard deviation of SNRs and CNRs for GOCTA, SVOCT, UHS-OMAG and SSADA are 25±2, 23±2, 23±2, 22±1 and 14±2, 9±2, 11±3, 9±2, respectively. The results demonstrate that the proposed GOCTA method can provide comparable image quality.

As the results show, the SNRs and CNRs obtained by GOCTA are slightly higher than the other three algorithms. Without intending to be limited by theory, it is suspected that the reason for this improvement may be that the proposed algorithm uses a large range of frequency components (the sample information within depth range of $\delta Z - \Delta z/2$ to $\delta z + \Delta z/2$ in spatial domain) to calculate the blood flow information, which is more robust compared to the other three algorithms where only the sample information at the same depth is used and then perform maximum (mean) projection to generate en face microvascular images.

Example: Comparison of Data Processing Time for GOCTA and Other Algorithms

It is noted that that the commercial system output of SSADA images as shown in FIGS. 8B and 9B are based on FIGS. 8F and 9F, upon which corrections of motion artefact, sub-regional registration, and additional contrast enhancement are applied to two directions (x and y) of scanning dataset. The GOCTA images quality, both qualitatively and quantitatively, were found to be at least on par (or possibly superior) in comparison with the unidirectional scan results of SSADA. These subsequent data processing techniques on the commercial system are proprietary and thus not compared for computational complexity and time. In principle, these would be equivalent when applied to any en face dataset.

A key advantage of the present GOCTA method is the speed of processing. The datasets were processed on the same computer using published SVOCT, UHS-OMAG, and SSADA algorithms, in MatLab®. It is noted that in order to obtain datasets used to post-process the commercial SSADA image, both scanning in the x and y directions were performed and the SSADA algorithm must be repeated, which doubled the numerical processing time. The data processing was accomplished on a laptop (CPU: i7-4720HQ, memory: 16 G, GPU: NVIDIA Geforce (GTX 970M), operating system: windows 8.1). The data processing time for each 2 B-scans from the same position was calculated and the results are shown in FIG. 10A.

Of the computational methods that were tested and compared, only the GOCTA and AGOCTA methods were able to directly provide en face microvascular images without needing to perform an FFT. In SVOCT, UHS-OMAG, and SSADA, the steps of k-space resampling, dispersion compensation and FFT are computationally costly, resulting in 6, 4, and 20 times slower than GOCTA, respectively. Since GOCTA does not require resampling, dispersion compensation, and FFT, the total processing time decreases dramatically.

Using GPU-based parallel computing library on Matlab, the data processing time was also measured for the entire 3D (608×2048×304) dataset and the results are shown in FIG. 10B. It is noted that these results are only illustrative as additional GPU algorithm optimization is possible outside of the Matlab programming environment, however, the present comparison serves to show the different components of the overall computational can be GPU accelerated to different extents. The data processing was simulated on a GPU, assuming the acquired interference fringes were transferred to GPU frame by frame (2048×304), as each B-mode image dataset became available. According to such an implementation, the initial surface profile detection would be performed first in order to obtain the necessary approximation of the tissue surface (e.g. spherical in the case of the retinal surface), and the GOCTA method, as well the other processing algorithms, were performed for comparison. It is noted that in the case of only using three A-scans for surface profiling, the processing time for these three A-scans is negligible with respect to the overall processing time.

It is also noted that the steps of k-space resampling, numerical dispersion compensation, and image alignment required both matrix amplitude and matrix indices adjustment using algorithms such as spline fitting, a GPU-based parallel computing Matlab library was not readily available. Hence these methods were kept as CPU operations in the current analysis, but could be further improved outside of the Matlab environment. Nevertheless, since the overall computational complexity of GOCTA was simpler than SVOCT, OMAG, and SSADA, the above analysis illustrated that the GOCTA method is indeed faster to compute under GPU acceleration. In this work, k-space resampling was accomplished by using cubic spline interpolation.

Example: Improvement of Sensitivity for Human Eye Imaging for GOCTA Method with Texture Removal To verify the improvement of sensitivity using the modified GOCTA method involving improved surface characterization (using an approximately uniform distribution of a set of A-lines) and texture noise reduction, two local regions were scanned (6×6 mm$^2$) on a healthy volunteers optical nerve head region and fovea region for data processing and comparison. The results are shown in FIGS. 11A-11H. By subtracting the optimized images FIG. 11E-11F by the regular images FIG. 11C-11D, the differential images FIG. 11G-11H were obtained and showed the extra microvascular information extracted by the refined GOCTA method (that includes texture removal). The results demonstrated that the improved GOCTA method could achieve even a higher sensitivity.

To evaluate the performance of the proposed surface calculation method, the calculated surface data was plotted (red curves) on the cross sectional structural images at the positions of 0 mm, 0.7 mm, 1.3 mm, 2.0 mm, 2.6 mm, 3.3 mm, 4.0 mm, 4.6 mm, 5.3 mm and 6.0 mm, as shown in FIGS. 12A-12T. It could be found that the surface data fit well with the structural images, except for some local areas with high curvature (marked by yellow arrows). Due to a large depth range that was used in the GOCTA method to calculate en face microvascular images, the depth shifts at the marked positions by yellow arrows could be covered.

Example: Microvascular Images of Sub Spectral Band and Sub Sampling Band

Figure 14:
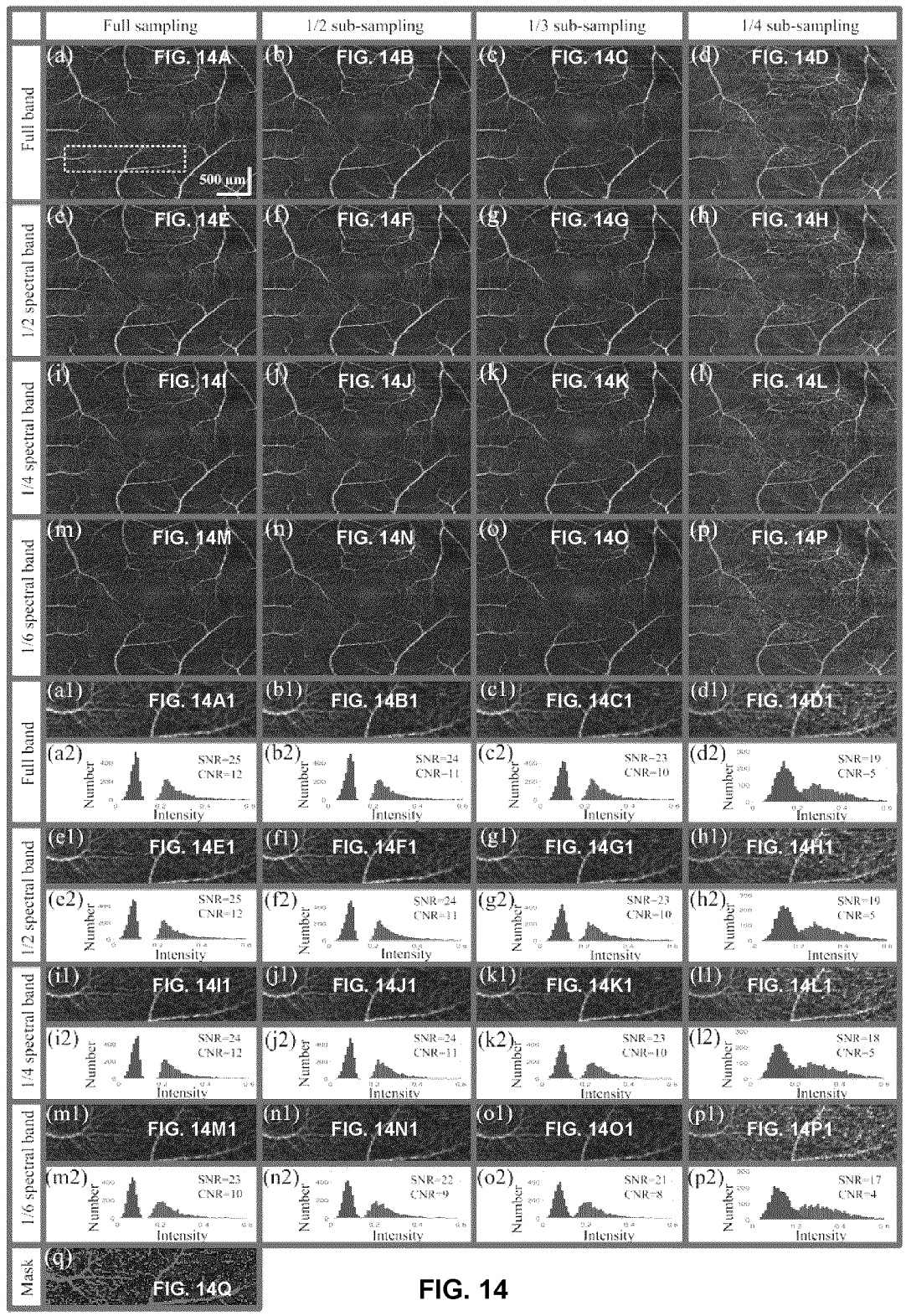
FIGS. 14A-14Q show microvascular images of sub spectral band and sub sampling band on fovea region. (a)-(p) are en face images with different spectral bands and different sampling bands. (a1)-(p1) are the zoomed local images in the marked region by a dashed rectangle in (a)-(p). (a2)-(p2) are the histograms of the pixel intensities in (a1)-(p1) covered by mask (q), where red and blue represent dynamic and static signals, respectively. (a)-(p) share the same scale bar.

To investigate the performance of sub spectral band and sub sampling band, a local region (3×3 mm$^2$) of both optical nerve head region and fovea region was scanned on a healthy volunteers retina. The en face microvascular images with different spectral bands and different sampling bands were calculated and are shown in FIGS. 13A-13Q (optical nerve head region) and FIGS. 14A-14Q (fovea region). In comparing these images, it could be found the images quality reduced as the decrease of spectral band and sampling band, and the image of ¼ spectral band and ½ sub sampling band had almost the same SNR and CNR with the image of full spectral band and full sampling band.

Figure 15A:
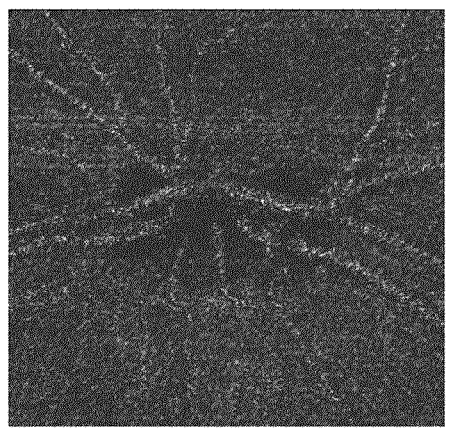
FIGS. 15A and 15B show the "lost" microvascular information by ¼ spectral band and ½ sampling band compared to full band. The "lost" microvascular information shown in (a) and (b) are obtained by subtracting FIG. 13(a) by FIG. 5(j) and FIG. 6(a) by FIG. 6(j), respectively.
Figure 15B:
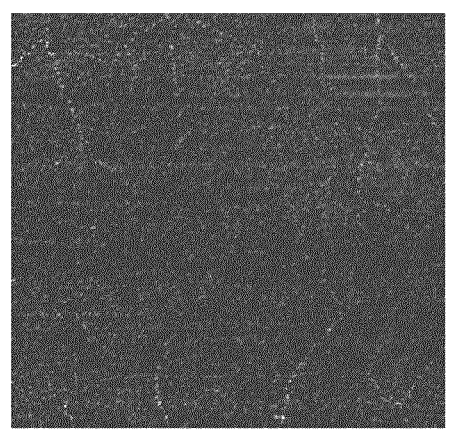

To estimate the loss of microvascular information, the full spectral and sampling band images were subtracted by ¼ spectral band and ½ sampling band image and the results were shown in FIGS. 15A and 15B. FIGS. 15A and 15B show the differential images for optical nerve head region and fovea region, respectively. It was found that for the GOCTA method, ¼ spectral band and ½ sampling band of spectral fringes could be used to calculate en face microvascular images without significant degradation of image quality.

As shown above, the image quality and data processing time of regular GOCTA was compared to other three algorithms: SVOCT, OMAG and SSADA. To make fair comparisons, performed SVOCT and OMAG was also performed on the fringes of ¼ spectral band and ½ sampling band to calculate the microvascular images. SSADA was not performed for comparison, since the sub band fringes had only 256 pixels which was hard to be split into 4 segments. The results were shown in FIG. 16A-16J. The differential microvascular images FIGS. 16C, 16E, 16H and 16J were obtained by subtracting GOCTA images by SVOCT and OMAG images and, from these differential images, it could be found that the enhanced GOCTA method (using additional A-scan lines and texture removal) provided a higher sensitivity for extracting vascular information.

Figure 17:
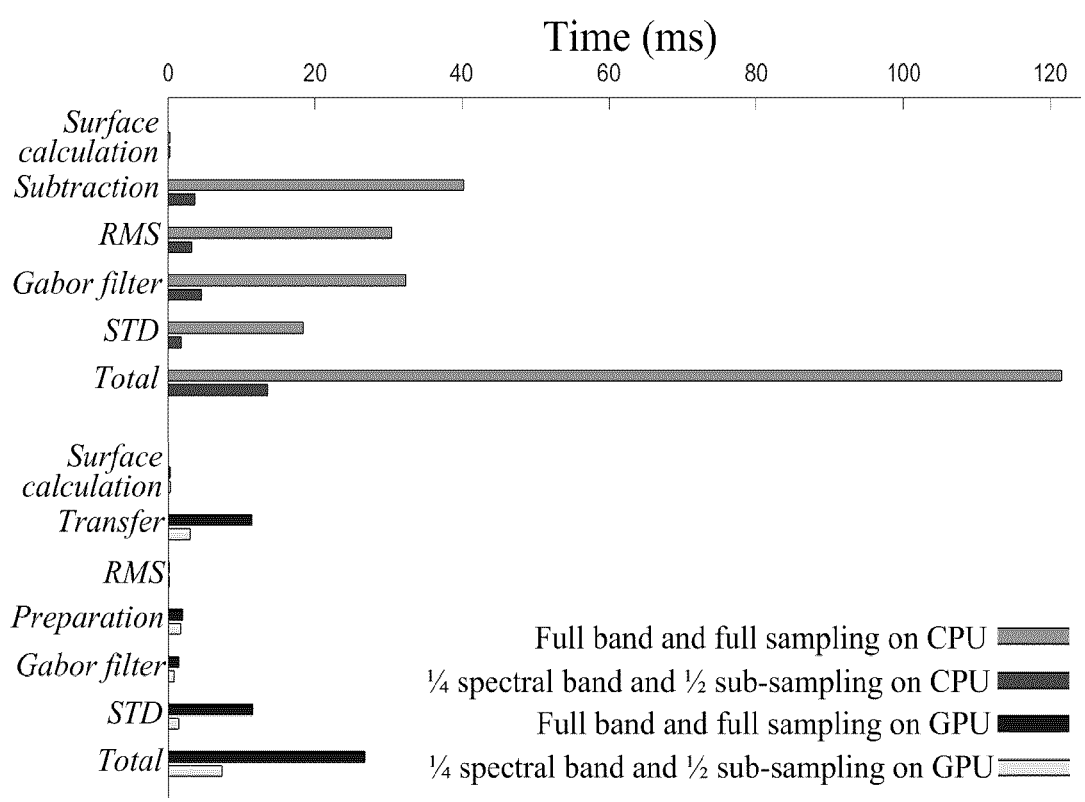
FIG. 17 plots the data processing time of each step of GOCTA for two B-scans from the same position on both CPU and GPU. Sum is the calculation of the total energy of the two A-scans. Transfer is the process of transferring data from host memory to GPU memory. Preparation is some steps to get the convolution prepared. On GPU processing, the time for subtraction of two B-scans was covered by preparation time since it is too small to show in the figure.

The data processing time was also analyzed for the GOCTA method using both CPU and GPU processing. Data processing was performed for different spectral bands and different sampling bands on a laptop (CPU: i7-4720HQ, memory: 16 G, GPU: NVIDIA Geforce (GTX 970M), operating system: windows 8.1) using GOCTA in MatLab®. The data processing time for each step of GOCTA on two B-scans from the same position was shown in FIG. 17. It is noted that the time for the surface calculation was obtained by dividing the entire time by the scanning steps in slow scanning direction. When measuring data processing time on GPU, surface calculation was also performed on CPU. Since GPU processing had the capability of parallel processing, the time for each step was very small. To improve the accuracy of time measurement on GPU, the processing time for each step was measured by performing this step on 100 pairs of two B-scans and then calculating the mean value. It could be found, by using ¼ spectral band and ½ sampling band, the data processing speed was improved by almost 8 and 4 times on CPU and GPU, respectively.

The processing time was also measured for the entire 3D data set on CPU and GPU processors, respectively, and the results were shown in FIG. 18. It could be found, by using ¼ spectral band and ½ sampling band, the data processing speed was improved by almost 9 and 4 times on CPU and GPU, respectively.

Example: Use of AGOCTA Method for Skin Angiography

In this present example, skin imaging experiments were performed on a commercial SSOCT system (VivoSight, Michelson Diagnostics, Kent, UK). The light source (Axsun Technologies, USA) had a center wavelength of 1305 µm and operated at a scanning rate of 20 kHz. The axial and lateral resolutions of this system were 10 µm and 7.5 µm, respectively. During scanning, each position was scanned twice and 240×1300 A-scans over 6×6 mm$^2$ were acquired.

Figure 19A:
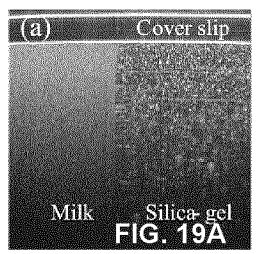
FIGS. 19A-19I plots images of phantom experiments. (a) Cross sectional structural image. (b)-(d) The en face flow images obtained by cmOCT, SVOCT and AGOCTA, respectively, at the marked depth (660 µm) by a dashed red line in (a). All three images had same depth range of 300 µm. (e)-(g) are the histograms of the marked regions (dashed rectangle: dynamic signal, solid rectangle: static signal) in (b)-(d). In the histograms, dynamic and static signals were marked as red and blue, respectively. (b)-(d) shared the same scale bar.
Figure 19B:
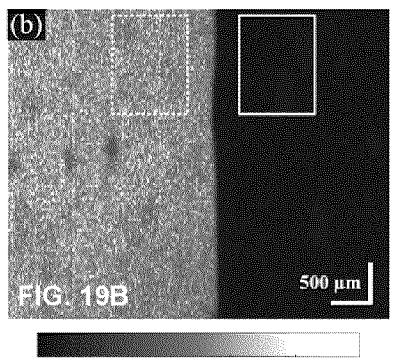
Figure 19C:
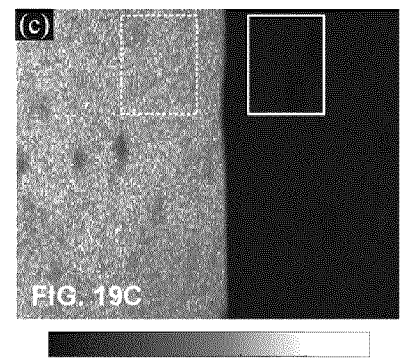
Figure 19D:
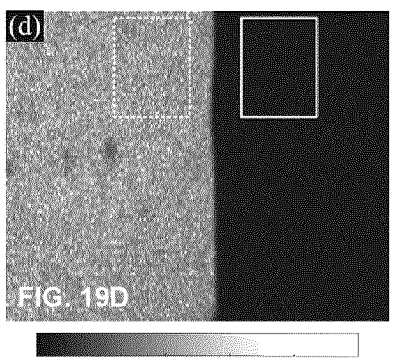

The performance of an example implementation of the AGOCTA method was tested using a phantom experiment and compared the results to cmOCT and svOCT. The phantom consisted of half milk (5%) and half silica-gel with the structural image as shown in FIG. 19A. FIGS. 19B-19D were the normalized en face images obtained by cmOCT, SVOCT and AGOCTA, respectively. In cmOCT and SVOCT, mean intensity projection (MIP) was performed to calculate the en face dynamic flow images. The surface data was not calculated in this case due to the planar surface of the cover slip. The correlation values in cmOCT were calculated by $$cmOCT(x,z) = 1 - \frac{\sum_{i=0}^{M-1}\sum_{j=0}^{P-1}[I_{2N-1}(x+i,z+j)-\bar{I}_{2N-1}][I_{2N}(x+i,z+j)-\bar{I}_{2N}]}{\sqrt{\sum_{i=0}^{M-1}\sum_{j=0}^{P-1}[I_{2N-1}(x+i,z+j)-\bar{I}_{2N-1}]^2}\sqrt{\sum_{i=0}^{M-1}\sum_{j=0}^{P-1}[I_{2N}(x+i,z+j)-\bar{I}_{2N}]^2}}, \quad (8)$$

where i and j are the pixel index, M and P are the correlation window size and they were both set to be 3 in this work. $I_{2N-1}$ and $I_{2N}$ are the two frames of intensity based structural images from the same position, $\bar{I}$ is the mean value in the correlation window. All of the resultant cross-sectional correlation images were multiplied by the corresponding structural images to suppress the background noise.

Figure 19E:
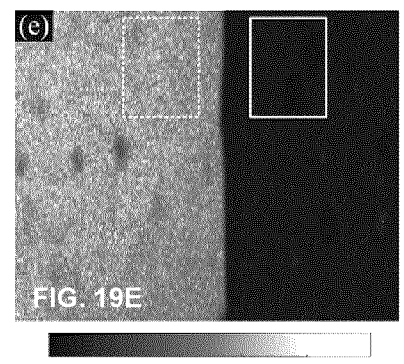
Figure 19F:
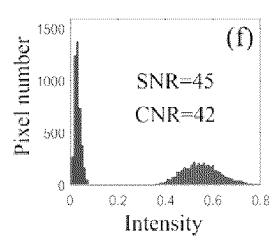
Figure 19G:
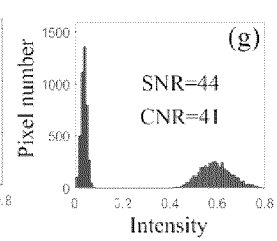
Figure 19H:
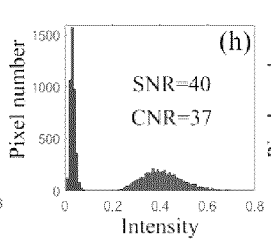
Figure 19I:
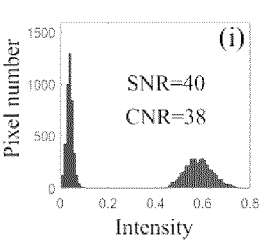

Signal to noise ratio (SNR) and contrast to noise ratio (CNR) were calculated for quantitative comparisons. The regions marked by the dashed rectangles (dynamic signal) and solid rectangles (static signal) were utilized for SNR and CNR calculations, with comparison histograms for the three algorithms as shown in FIGS. 19E-19G. It is noted that the SNRs and CNRs obtained by these three algorithms were similar.

Example: Results of AGOCTA on a Healthy Volunteers Palm

Figure 20A:
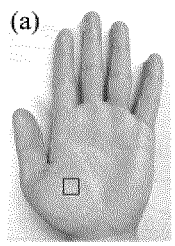
FIGS. 20A-20K show microvascular images of a local region on a healthy volunteers palm. (a) Photograph of the volunteers hand. The marked region (6×6 mm) was scanned. (b) The estimated surface curvature. (c) The mask for blood flow signals (red) and background (blue). (d)-(f) The en face microvascular images calculated by cmOCT, SVOCT and AGOCTA, respectively. These three images were at the depth of 550 to 850 µm from skin surface. The correlation window size of 3×3 pixels was used in cmOCT. (g)-(i) are the histograms of the intensity values within the mask (c), where dynamic and static signals were marked as red and blue, respectively. (c)-(f) shared the same scale bar.
Figure 20B:
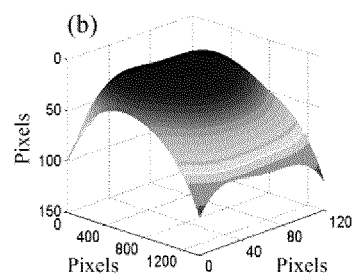
Figure 20C:
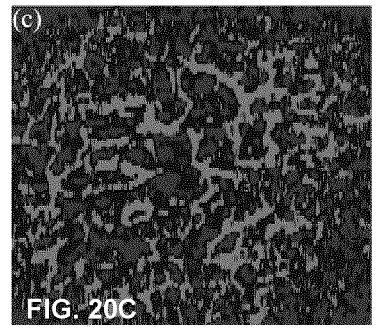
Figure 20D:
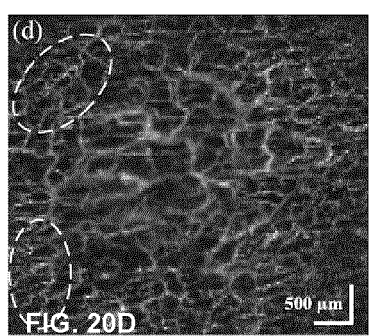
Figure 20E:
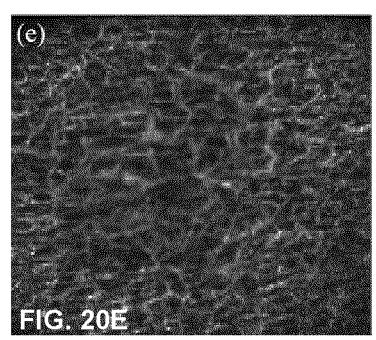
Figure 20F:
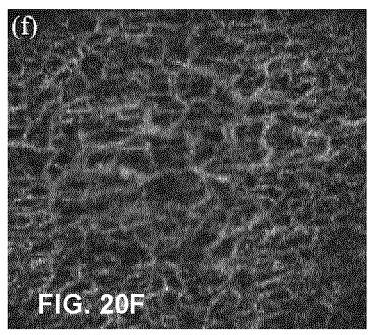
Figure 20G:
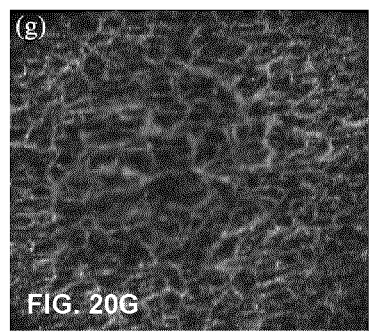
Figure 20H:
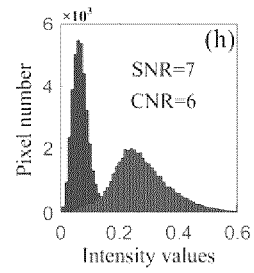
Figure 20I:
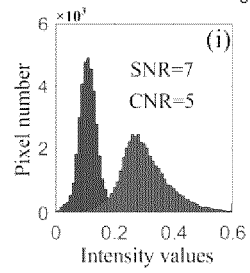
Figure 20J:
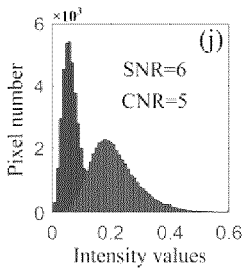
Figure 20K:
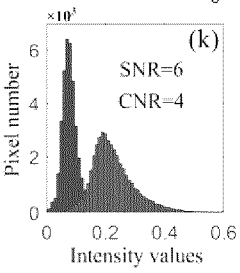

A local region on a healthy volunteers palm was also scanned, and the en face microvascular images were calculated by performing cmOCT, SVOCT and AGOCTA algorithms on the same dataset, respectively. In this region, regular AGOCTA and SVOCT were performed to calculate en face microvascular images since texture noise was not found. The results are shown in FIGS. 20A-I. FIG. 20A shows the photography of the volunteer's palm with the marked region (6×6 mm) as scanned. FIG. 20B was the calculated surface data. By thresholding the en face microvascular images, the mask for blood flow signals and background was obtained, as shown in FIG. 20C, where the red and the blue represented blood flow and background signals, respectively. FIGS. 20D-20F show the microvascular images obtained by cmOCT, SVOCT and AGOCTA, respectively. In cmOCT, the correlation widow size was 3×3 pixels and the obtained cross-sectional correlation coefficient images were multiplied by the intensity based structural images to suppress the background noise. The correlation window decreased the lateral resolution, resulting in the discontinuity of small blood vessels, as shown in the regions marked by dashed ellipses in FIG. 20D. The intensity values covered by the mask FIG. 20C were used to calculate SNR and CNR for quantitative comparison, with the histograms as shown in FIGS. 20G-I. These three algorithms provided similar SNRs and CNRs.

To verify the accuracy of the estimated surface, FFT was performed on uniformly distributed 12 cross sectional images to calculate the structural images at positions of 0.5 mm, 1.0 mm, 1.5 mm, 2.0 mm, 2.5 mm, 3.0 mm, 3.5 mm, 4.0 mm, 4.5 mm, 5.0 mm, 5.5 mm and 6.0 mm in slow scanning direction, the results were shown in FIGS. 21A-L, where the red curves show the estimated surface data. It was found that, apart from some local high frequency components (marked by the white arrows), the obtained curves matched the skin's surface well. The accuracy of surface data could be improved by increasing the size of the matrix used for calculating the original surface data uniformly distributed on xy plane.

Example: Comparison of Data Processing Time for AGOCTA and Other Algorithms

Figure 22:
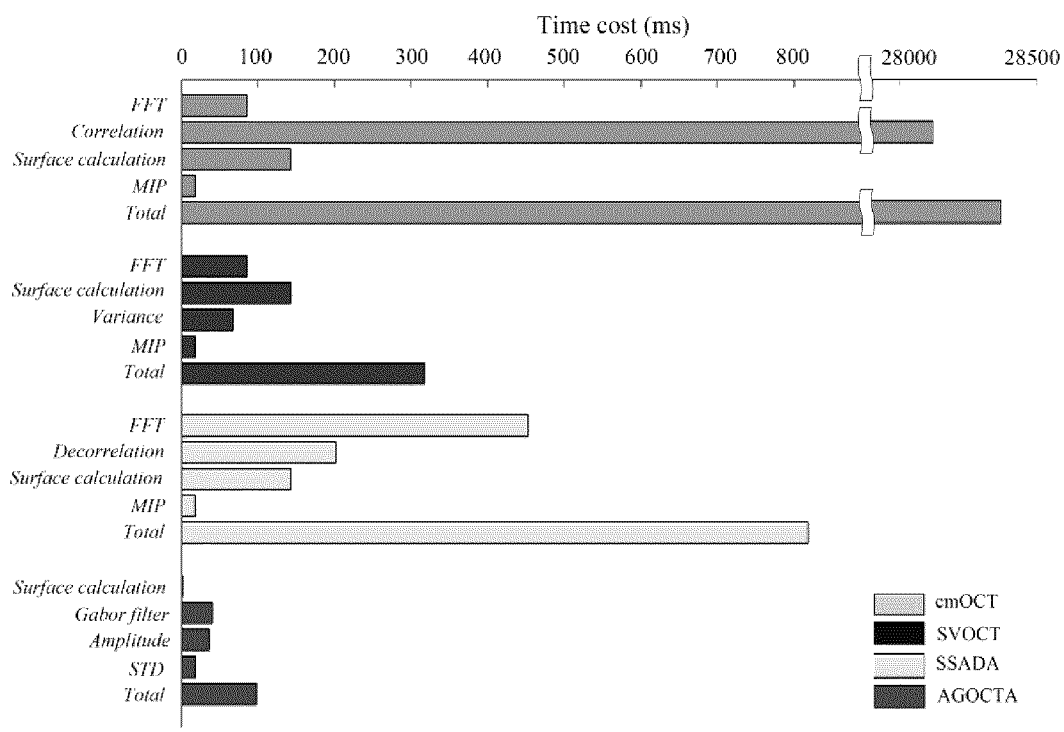
FIG. 22 plots a comparison of data processing time for two B-scans from the same position on CPU. Fast Fourier Transform (FFT) and mean intensity projection (MIP) were performed in cmOCT and SVOCT. In the AGOCTA method, the time for Hilbert transform and amplitude calculation was included in the standard deviation (STD) time.

Similar to the GOCTA method, the main advantage of the AGOCTA method is the data processing speed. Data processing was performed on a laptop (CPU: i7-4720HQ, memory: 16 G, GPU: NVIDIA Geforce (GTX 970M), operating system: windows 8.1) using the published cmOCT, SVOCT and the proposed AGOCTA in MatLab®. To make the comparison convincing, the data processing time was measured for 2 B-scans from the same position on CPU and GPU, respectively. The results were shown in FIG. 22 and FIG. 23, respectively. During data processing, the en face microvascular images were calculated within the depth range of 10% of the total OCT ranging depth, resulting in a convolving kernel with length of 16 pixels. In FIG. 22, the surface data for each frame was calculated by the following steps in both cmOCT and SVOCT: 1) median fitter and threshold structural images; 2) index the position of the first non-zero value in each Aline; 3) perform a 4th order of polynomial fitting to smooth the curve. To make a fair comparison, the surface calculation time for the AGOCTA method was obtained by dividing the whole surface calculation time by the number of scanning steps in slow scanning direction. Using the AGOCTA method, data processing speed was improved by nearly 187 and 2 times on CPU compared to cmOCT and SVOCT, respectively.

Figure 23:
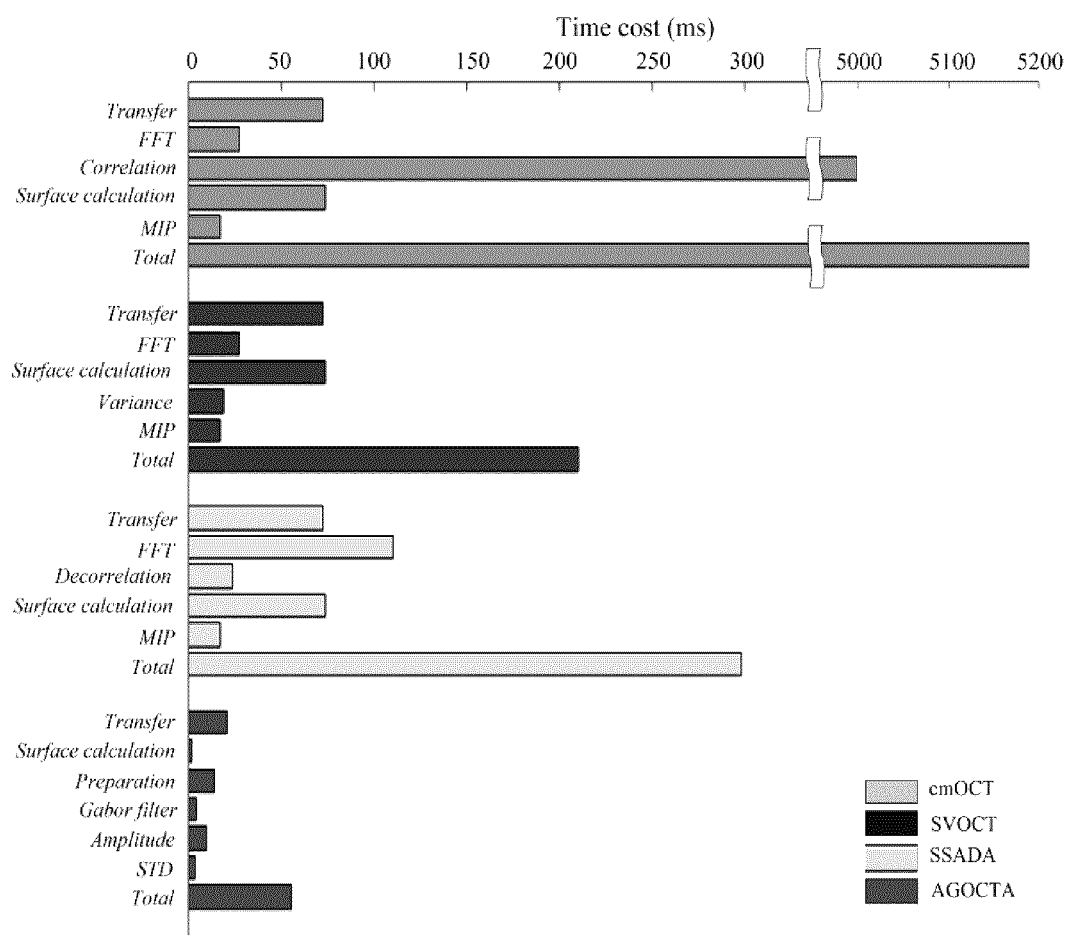
FIG. 23 plots a comparison of data processing time for two B-scans from the same position on GPU. "Transfer" in this context refers to the transfer of data from host memory to GPU memory.

In FIG. 23, a GPU based parallel computing library was employed on Matlab for data processing and measured the time. In the step of surface calculation, only image filtering was performed on GPU for cmOCT and SVOCT, while for the AGOCTA method, the entire step was performed on CPU. The data processing speed was improved 38 and 1.5 times on GPU compared to cmOCT and SVOCT, respectively.

Figure 24:
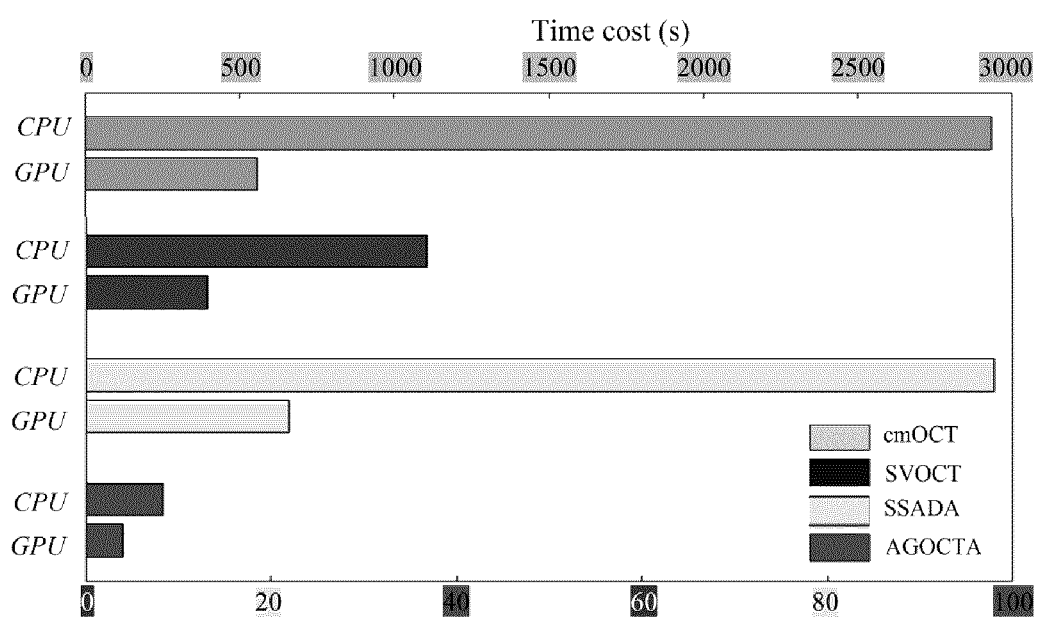
FIG. 24 plots a comparison of data processing time for entire 3D data. The upper time axis is for cmOCT and the lower one is for SVOCT and AGOCTA.

The data processing time was also measured for the entire 3D dataset on both CPU and GPU, the results were shown in FIG. 24. Here, the data processing was simulated under real time imaging mode by calculating the acquired interference fringes frame by frame (1024×1365), as each B-mode image dataset became available on both CPU and GPU. It was found, on both CPU and GPU, AGOCTA provided the fastest data processing speed.

Example: Texture Noise Removal on Human Skin

To test the performance of the example texture noise removal method disclosed above, a right rear region on a healthy volunteers left palm was scanned, where the palm print was strong. SVOCT and AGOCTA were performed on the fringe data to calculate en face microvascular images, respectively. The depth ranges were changed (180 μm) in this case to calculate the images within three different depth ranges and the results were shown in FIGS. 25A-25V. It was found that after removing texture pattern, more blood flow signals (as shown in the differential images) were extracted and the quality of blood vessel's image was improved.

Example: In Vivo Imaging on a Hereditary Hemorrhagic Telangiectasia (HHT) Patient's Lesion Using AGOCTA Method In addition to volunteer imaging, the present AGOCTA method was employed in HHT patients in lesion imaging, as part of a larger clinical study. Hospital Research Ethics Board approval was obtained in these patients before and after topical beta-blocker treatment. One pre-treatment imaging results are presented in this example to demonstrate that the AGOCTA method could be performed in the clinic setting for imaging microvascular, as shown in FIGS. 26A-26J. FIGS. 26(e) and (h) were obtained by SVOCTA while FIGS. 26 (f) and (i) were obtained by the AGOCTA method, and texture noise was removed in (e) and (f). In comparison of these four images, the present method was able to remove texture noise on skin lesion and provide a better quality of microvascular images. In comparison of FIGS. 26(g)-(i), it could be found that the AGOCTA method provided a slightly better contrast for blood vessels, especially the region marked by the dashed white circles. FIGS. 26(j)-(l) were the histograms of the intensity values covered by the mask FIG. 26(c) for SNR and CNR comparisons.

Example: Results of AGOCTA on Sub Spectral and Sub Sampling Bands

As in the GOCTA method described above, the AGOCTA method was also performed on the sub bands of spectral fringes to accelerate the data processing speed, and a local region (6×6 mm2) on a healthy volunteers palm was scanned and processed to demonstrate the performance. Data processing time and microvascular images and of sub bands are shown in FIG. 27 and FIGS. 28A-28M, respectively. The statistic of the intensity values in a region marked by a dashed white rectangle in FIGS. 28(a)-(l) were calculated for quantitative comparisons, and it was found that the image of ½ sub sampling band and ½ sub spectral band was comparable to the full band images. However, the data processing time was decreased by almost 6 times on CPU and almost 4 times on GPU, as shown in FIG. 27. Therefore, the AGOCTA method was performed on the fringes of ½ sub spectral and ½ sub sampling to calculate microvascular images in preceding Examples.

Example: Microvascular Images of Scalp on a Healthy Volunteer

To further test the performance of the texture artifact removing in the AGOCTA method, a local region (6×6 mm2) of scalp was scanned on a healthy volunteer. Before scanning, the local region of scalp was shaved to remove hairs. The obtained microvascular images were shown in FIGS. 29E-29J. Comparing FIGS. 29(e)-(g) with FIGS. 29(h)-(j), it was found the texture artifacts (marked by dashed yellow circles) caused by hair follicle were removed by the proposed method. The results demonstrated that the AGOCTA method, with optional texture removal, may be performed prior to or during a hair transplant to improve the possibility of survival of new hair donor site by selecting the hair follicles with richer capillaries, as well as by selecting the better recipient site with better capillary network yet not injuring the microvessels during the transplant process.

Example: Impact of Sub Spectral Band Sampling and Skipped Convolution Processing on Image Quality FIGS. 30A-30I show images obtained using different example implementations of the GOCTA algorithm in the example case of retinal imaging. As can be seen in the figures, the image quality is maintained when using the "skipped convolution" method and/or the spectral-sub band method.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of generating an en face angiography image via optical coherence tomography, the method comprising:
    employing a spectral domain or swept source optical coherence tomography system to scan a spatial region comprising a tissue surface and to detect at least a first spectral interferogram frame and a second spectral interferogram frame;
    processing the first spectral interferogram frame and the second spectral interferogram frame via subtraction to generate a differential spectral interferogram frame;
    performing a convolution of a Gabor filter with the differential spectral interferogram frame, thereby obtaining a Gabor-convolved differential spectral interferogram frame, wherein the Gabor filter is computed, on a per-pixel basis, based on an estimated depth of the tissue surface; and
    processing the Gabor-convolved differential spectral interferogram frame to generate the en face angiography image, wherein the Gabor-convolved differential spectral interferogram frame is processed in the absence of performing a fast Fourier transform and k-space resampling.

2. The method according to claim 1 wherein a given pixel of the en face angiography image is generated by calculating, for a respective pixel of the Gabor-convolved differential spectral interferogram frame, a measure quantifying a spectral statistical dispersion.

3. The method according to claim 1 wherein a given pixel of the en face angiography image is generated by calculating, for a respective pixel of the Gabor-convolved differential spectral interferogram frame, measure based on a spectral standard deviation.

4. The method according to claim 1 wherein the estimated depth of the tissue surface, for a given transverse pixel of the differential spectral interferogram frame, is obtained from a spatial characterization of the tissue surface, and wherein the spatial characterization of the tissue surface is determined by:
    performing a plurality of A-scans through different locations of the tissue surface and detecting respective interferograms;
    processing the interferograms to determine a respective surface depth value at the locations; and
    fitting the surface depth values to a functional form to obtain the spatial characterization the tissue surface.

5. The method according to claim 4 wherein the tissue surface is a retinal surface, and wherein the functional form is a sphere.

6. The method according to claim 4 wherein the tissue surface is skin, and wherein the functional form is a polynomial equation.

7. The method according to claim 1 further comprising computing a plurality of en face angiography images, and generating a video display based on the plurality of en face angiography images as a video.

8. The method according to claim 1 wherein at least a portion of the processing is performed using a graphics processing unit.

9. The method according to claim 1 wherein, for at least one pixel of the differential spectral interferogram frame, a sub-band of the differential spectral interferogram is selected and employed when performing the convolution, thereby reducing a computation time associated with the convolution.

10. The method according to claim 1 wherein a number of pixels of the differential spectral interferogram frame are skipped between successive steps when performing the convolution, and wherein the number of pixels is less than the kernel of the Gabor filter.

11. The method according to claim 1 wherein the convolution is performed such that each pixel of the differential spectral interferogram frame is employed only once.

12. The method according to claim 1, wherein the en face angiography image is a first en face angiography image, the method further comprising:
    computing absolute values of the first spectral interferogram frame and the second spectral interferogram frame, thereby obtaining a first absolute spectral interferogram frame and a second absolute spectral interferogram frame;
    computing the sum, over spectral pixels, of the first absolute spectral interferogram frame and the second absolute spectral interferogram frame, thereby obtaining a summed absolute spectral interferogram frame; and
    obtaining a texture-noise-suppressed en face angiography image by dividing the first en face angiography image by the summed absolute spectral interferogram frame.

13. A system for generating an en face angiography image via optical coherence tomography, the system comprising:
    a spectral domain or swept source optical coherence tomography system; and
    control and processing circuitry operatively coupled to the optical coherence tomography system, the control and processing circuitry comprising a processor and a memory, wherein the processor is configured to execute instructions stored in the memory for performing the steps of:
        controlling the optical coherence tomography system to scan a spatial region comprising a tissue surface and to detect at least a first spectral interferogram frame and a second spectral interferogram frame;
        processing the first spectral interferogram frame and the second spectral interferogram frame via subtraction to generate a differential spectral interferogram frame;
        performing a convolution of a Gabor filter with the differential spectral interferogram frame, thereby obtaining a Gabor-convolved differential spectral interferogram frame, wherein the Gabor filter is computed, on a per-pixel basis, based on an estimated depth of the tissue surface; and
        processing the Gabor-convolved differential spectral interferogram frame to generate the en face angiography image, wherein the Gabor-convolved differential spectral interferogram frame is processed in the absence of performing a fast Fourier transform and k-space resampling.

14. The system according to claim 13 wherein the control and processing circuitry is configured such that a given pixel of the en face angiography image is generated by calculating, for a respective pixel of the Gabor-convolved differential spectral interferogram frame, a measure quantifying a spectral statistical dispersion.

15. The system according to claim 13 wherein the control and processing circuitry is configured to compute a plurality of en face angiography images, and generate a video display based on the plurality of en face angiography images as a video.

16. The system according to claim 13 wherein the control and processing circuitry is configured at least a portion of the processing is performed using a graphics processing unit.

17. The system according to claim 13 wherein the en face angiography image is a first en face angiography image, and wherein the control and processing circuitry is configured to perform additional operations comprising:
    computing absolute values of the first spectral interferogram frame and the second spectral interferogram frame, thereby obtaining a first absolute spectral interferogram frame and a second absolute spectral interferogram frame;
    computing the sum, over spectral pixels, of the first absolute spectral interferogram frame and the second absolute spectral interferogram frame, thereby obtaining a summed absolute spectral interferogram frame; and
    obtaining a texture-noise-suppressed en face angiography image by dividing the first en face angiography image by the summed absolute spectral interferogram frame.

18. A method of generating an en face angiography image via optical coherence tomography, the method comprising:
    employing a spectral domain or swept source optical coherence tomography system to scan a spatial region comprising a tissue surface and to detect at least a first spectral interferogram frame and a second spectral interferogram frame;
    performing a convolution of a Gabor filter with the first spectral interferogram frame and the second spectral interferogram frame, thereby obtaining a first Gabor-convolved spectral interferogram frame and a second Gabor-convolved spectral interferogram frame, respectively, wherein the Gabor filter is computed, on a per-pixel basis, based on an estimated depth of the tissue surface;
    processing the first Gabor-convolved spectral interferogram frame and the second Gabor-convolved spectral interferogram frame to obtain amplitudes thereof, thereby obtaining a first Gabor-convolved spectral interferogram amplitude frame and a second Gabor-convolved spectral interferogram amplitude frame, respectively,
    processing the first Gabor-convolved spectral interferogram amplitude frame and the second Gabor-convolved spectral interferogram amplitude frame via subtraction to generate a differential Gabor-convolved spectral interferogram amplitude frame; and
    processing the differential Gabor-convolved spectral interferogram amplitude frame to generate the en face angiography image, wherein the differential Gabor-convolved spectral interferogram amplitude frame is processed in the absence of performing a fast Fourier transform and k-space resampling.

19. The method according to claim 18 wherein a given pixel of the en face angiography image is generated by calculating, for a respective pixel of the differential Gabor-convolved spectral interferogram amplitude frame, a measure quantifying a spectral statistical dispersion.

20. The method according to claim 18 wherein a given pixel of the en face angiography image is generated by calculating, for a respective pixel of the differential Gabor-convolved spectral interferogram amplitude frame, measure based on a spectral standard deviation.

* * * * *